United States Patent [19]

Cherksey et al.

[11] Patent Number: 4,950,739

[45] Date of Patent: Aug. 21, 1990

[54] MEMBRANE CALCIUM CHANNELS AND FACTORS AND METHODS FOR BLOCKING, ISOLATING AND PURIFYING CALCIUM CHANNELS

[75] Inventors: Bruce D. Cherksey, Hoboken, N.J.; Rodolfo R. Llinas; Mutsuyuki Sugimori, both of New York, N.Y.

[73] Assignee: New York University, New York, N.Y.

[21] Appl. No.: 219,105

[22] Filed: Jul. 14, 1988

Related U.S. Application Data

[63] Continuation-in-part of Ser. No. 154,845, Feb. 10, 1988, abandoned.

[51] Int. Cl.$^5$ .......................... C07K 3/20; C07K 15/08
[52] U.S. Cl. .................................... 530/350; 424/537; 424/538; 530/413; 530/858
[58] Field of Search ................... 424/95, 98; 530/350, 530/413, 858

[56] References Cited

PUBLICATIONS

Nevalainen, et al., Biomedical Research 8(2), 1987, pp. 89–93.
Adams, et al., Proceedings of the Australian Physiological and Pharmacological Society 7, 1976, p. 161p.
Cherksey, et al., Soc Neurosci Abstr 14(2), 1988, p. 901.
Strassberg, J. et al., Toxicon, 1:41, 1962.
Meadow, et al., Toxicon, 8:311–312.
Gregson, R. P. et al., Comp. Biochem. Physiol., 74C (1):125–132, 1983.
Scheumack, D. D., et al., Febs. LETTERS, 181 (1):154–156, 1985.
Jackson, H. et al., Neuroscience Abstracts, 1985 p. 107, 32.17 in Excitatory Amino Acids: Physiol. and Pharm.
Curtis, B. M., et al., Biochem. 1986, 25:3077–3083.
Adams, M. E., et al., Insect Neurophysiol. Pap. Int. Conf. Second, 1986, pp. 397–400.
Jackson, H. et al., Presynaptic Blockade of Transmission By A Protent, Long-Lasting Toxin From A. aperta, Soc. Neurosci. Abstr. 12:730, 1986.
Jackson, H. et al., In Excitatory Amino Acid Transmission, 1987 (Alan R. Liss, Inc.) pp. 51–54.
Miller, R. J., Science 235:46, 1987.
Bowers, C. W. et al., PNAS (U.S.A.) 84:3506, 1987.
Sugimori, M. et al., Soc. Neurosci. Abstr., 13:228, 1987.
Kerr, L. M., et al., Soc. Neurosci. Abstr. 13:102, 1987.
Lai, F. A. et al., Nature, 331–315, 1988.
Spence, J. Neurotoxins, Fundam. Clin. Adv. (Int'l Conf.), 1979.
Jackson, H. et al., TINS, 11:278, 1988.

Primary Examiner—Robert J. Warden
Assistant Examiner—Jill Johnston
Attorney, Agent, or Firm—Darby & Darby

[57] ABSTRACT

Nonpolypeptide factors isolated from the venom of funnel-web spiders are capable of binding calcium channel proteins. These nonpolypeptide factors are used to purify calcium channels and completely block voltage-dependant calcium conductance of cell membranes.

33 Claims, 24 Drawing Sheets

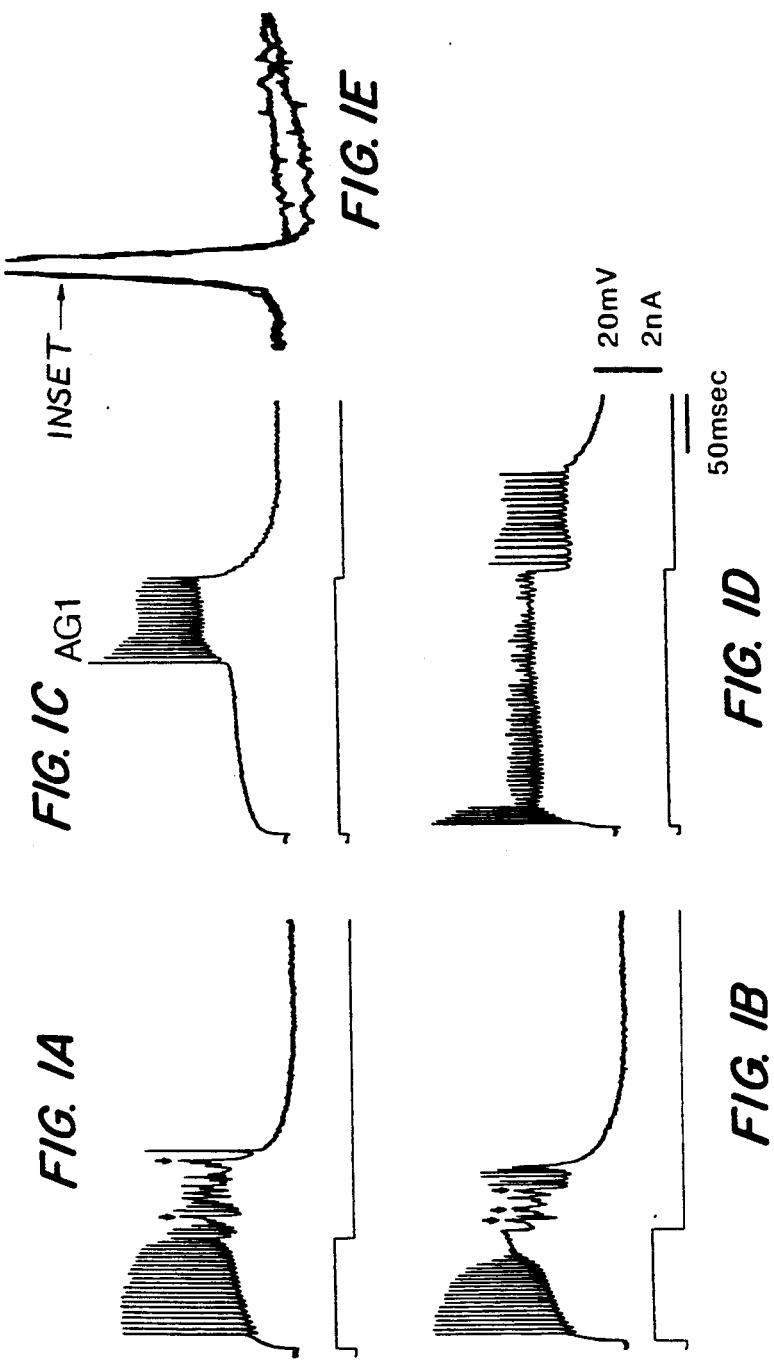

Hololena Curta
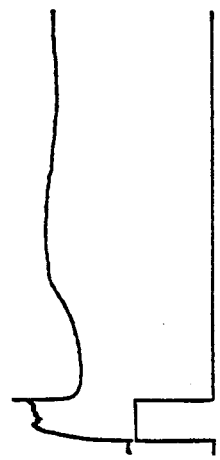
FIG. 2A
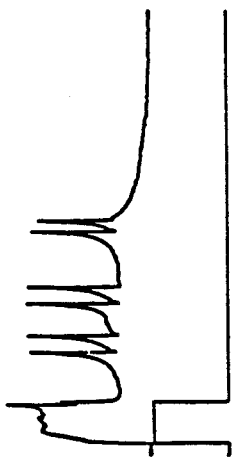
FIG. 2B
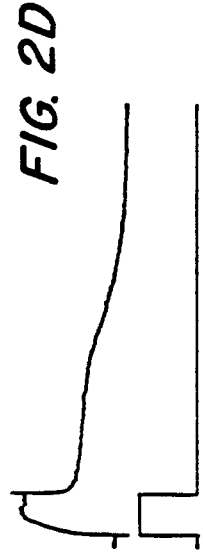
FIG. 2C
FIG. 2D
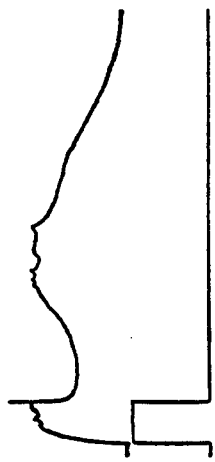
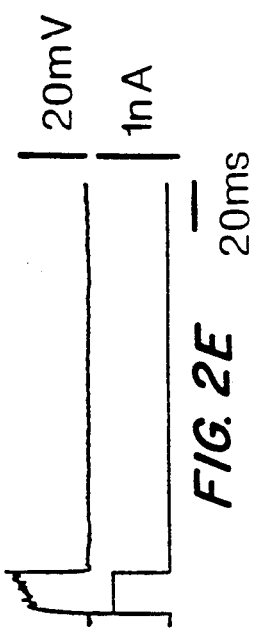
FIG. 2E
| 20mV
| 1nA
— 20ms

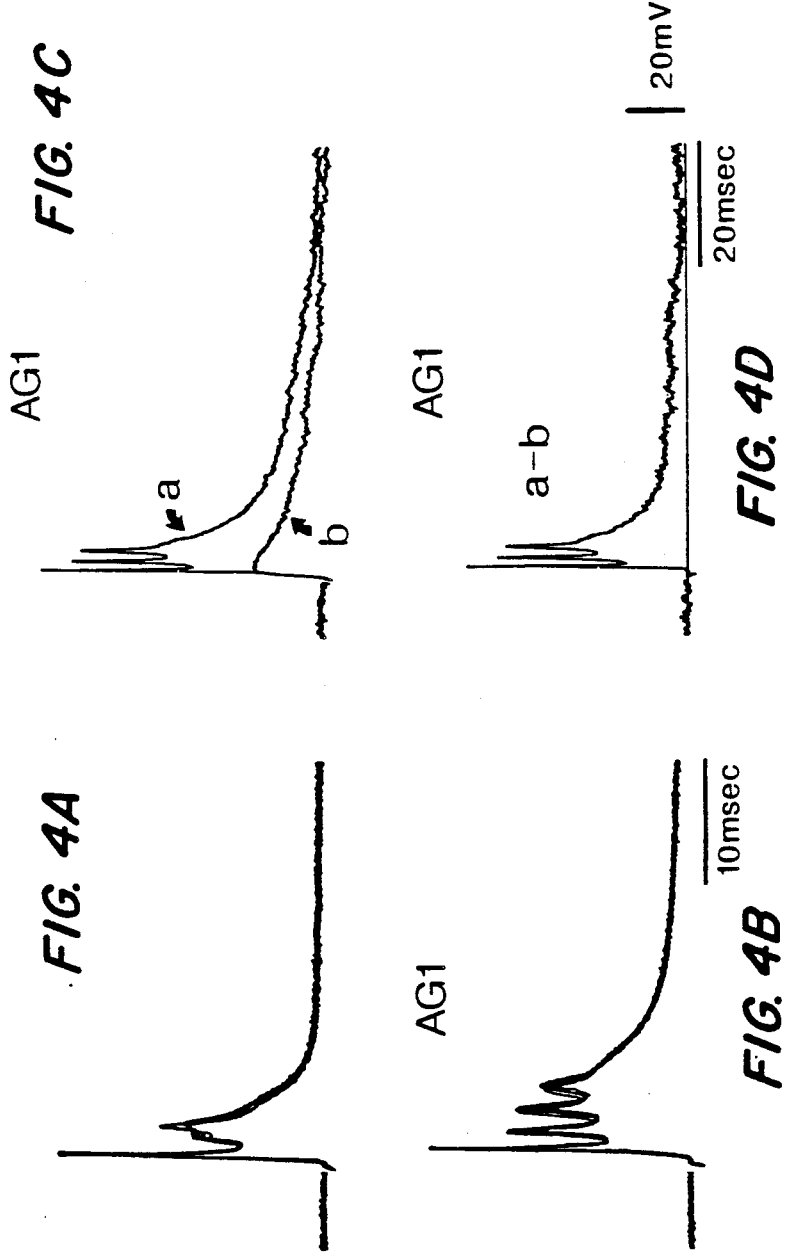

FIG. 10
250mm BaCl₂
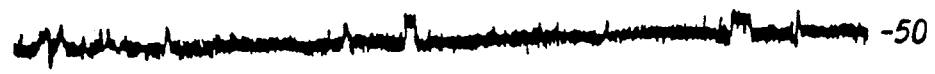 -50
 -90
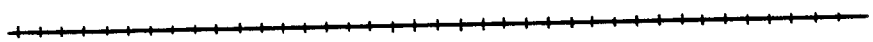
 $\frac{AG}{1:100}$ 50λ
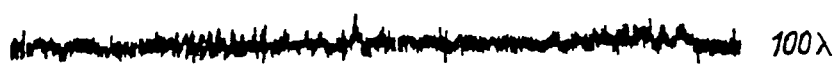 100λ
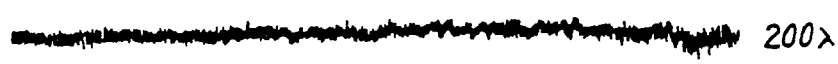 200λ

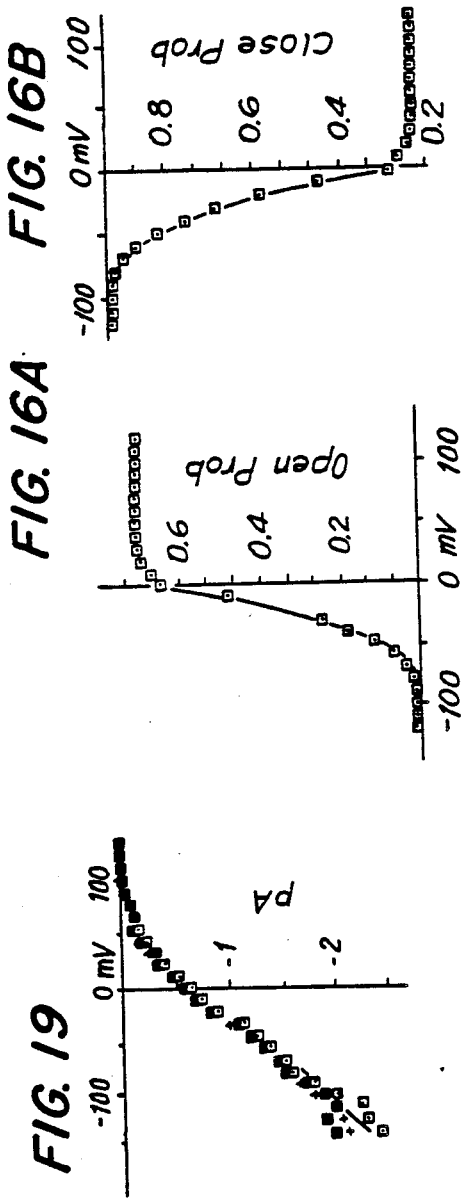
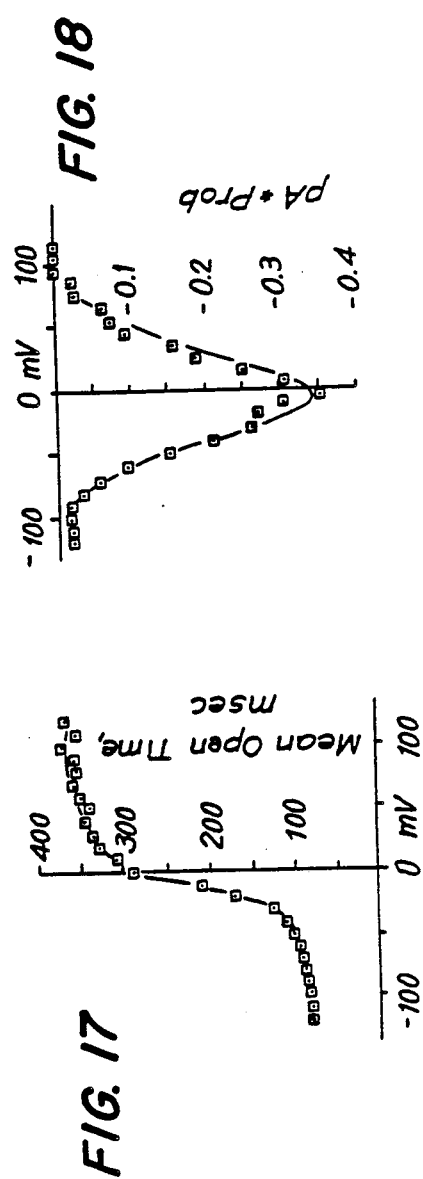
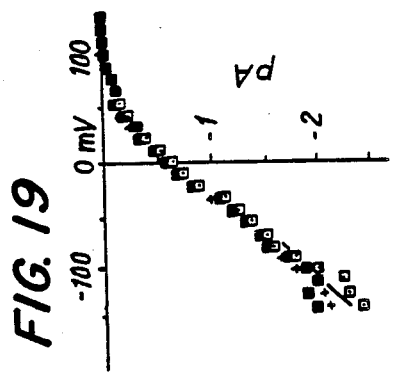
FIG. 16A  FIG. 16B  FIG. 17  FIG. 18  FIG. 19

ATX 1.6 ul/ml
10 min

MEMBRANE CALCIUM CHANNELS AND FACTORS AND METHODS FOR BLOCKING, ISOLATING AND PURIFYING CALCIUM CHANNELS

This is a continuation-in-part of copending application Ser. No. 154,845 filed on Feb. 10, 1988 in the names of the same inventors now abandoned.

BACKGROUND OF THE INVENTION

This invention relates to a cell membrane channel responsible for the so-called calcium conductance observed in neuronal and other cell membranes. This invention also relates to methods for purifying this channel and to factors and methods for regulating or blocking calcium conductance in cellular membranes.

Passive transport of charged particles across cell membranes, in response to an incremental change in an electrical field across the thickness of the cell membrane, is mediated (and, in substantial part, regulated) by membrane channel proteins.

In this discussion the terms "channel" and "channel protein" are used interchangeably without implying that a channel must necessarily consist of a single protein, although the channels which have been isolated are believed to be single proteins.

Most channel proteins are believed to mediate the transport of one ionic species with substantially higher specificity than transport of other ions. Although the existence of several channels has been experimentally demonstrated, fewer than ten channel proteins have been isolated. These include certain sodium and potassium channel proteins, the isolation of which has been described in the U.S. patent application Ser. Nos. 948,262 filed on Dec. 31, 1986 and 085,462 filed on Aug. 17, 1987 now abandoned both in the name of Bruce Cherksey the disclosures of which are incorporated by reference in their entirety.

Calcium channels have been shown to be responsible for highthreshold calcium conductance (HTCC) observed in responses to direct electric impulse (or synaptic) stimulation of neurons. This conductance is responsible for the calcium-dependent action potentials, especially in the dendrites (Llinas, R. and Sugimori, M. *J. Physiol.*, 305: 197-213, 1980). Calcium channels have also been shown to be responsible for a low-threshold calcium conductance (LTCC) which generates calcium-dependent spikes from a rather negative value of membrane potential (−65 mV). This LTCC spike often appears as a rebound depolarization following the after hyperpolarization potential which in turn follows the after depolarization potential due to the HTCC (Llinas and Yarom, *J. Physiol.*, 315: 549-567 and 569-584, 1981) Calcium channels are also involved in presynaptic transmitter release during synaptic transmission. Other cell types which possess such calcium channels include heart muscle fibers and endocrine cells.

Before the present invention, calcium channels were known to be structures spanning the lipid bilayer of the cell membrane and demonstrating high (though not exclusive) specificity for the transport of calcium ions through this membrane. Despite being the subject of considerable research effort, the types of calcium channel structures responsible for central neuron spike activity had not been isolated nor identified.

Among the reasons for the failure to isolate calcium channels was the unavailability of a material having at least one of the following properties:

ability to bind calcium channels specifically, tightly (with high affinity) and reversibly and to block the calcium conductance completely; and ability to be labelled by a fluorescent or other detectable marker while retaining the ability to bind the calcium channel thus making it possible to identify the location and quantify the occurrence of calcium channels on a cell membrane.

Previously known calcium channel blocking proteins such as nitrendipene, D600 (methoxyverapamil), doxorubicin hydrochloride, and quinidine could not be used for identification of the calcium channel because they bind the channel either nonspecifically or irreversibly or both. Also, some of these agents, notably dihydropyridines, do not recognize the type of channels responsible for calcium conductance in cerebellar neurons on which the experiments illustrating the present invention were conducted: R. J. Miller, infra.

Various natural toxins have recently become the focus of attention as potential tools for studying neuronal channels.

In the experience of the present inventors, conotoxin (a toxin from the venom of the marine snail *Conus geographicus*) which has been reported to block calcium channels (Miller, R. J., Science, 235:46, 1987) does not bind the calcium channels under investigation with sufficient affinity to be useful for channel isolation and purification.

Toxins present in or extracted from the venom of funnel-web spiders have also been the subject of substantial investigation. Sheumack, D. D., et al., FEBS 2237, 181:154 (1985) report the sequencing of a polypeptide toxin from the funnel-web spider Atrax robustus. The sequence of this polypeptide is said to contain 42 amino acid residues including several disulphide-bridged cysteine residues.

Venom and several chromatographic extracts from the venom of the *Agelenopsis aperta* spider, a common funnel-web spider indigenous to the continental United States, have also been under study.

A 6000 dalton molecular weight toxin derived from *A.aperta* venom was said to block synaptic transmission in chick brain stem neurons in a manner dependent on the extracellular calcium ion concentration: H. Jackson et al *Society for Neuroscience, Abstracts* 16th Annual Meeting, Washington, D.C. Nov. 9-14, 1986. The authors raise the possibility that the toxin might block either calcium channels or the synaptic release process itself and stated that the binding of the toxin appeared to be "very tight if not irreversible".

The same group of investigators have studied toxins from other spiders including the funnel-web spider *Hololena curta* and reported that one such toxin (estimated mw 5,000-10,000 daltons) blocks postsynaptic responses irreversibly. Another toxin said to be derived from *A.aperta* venom is also reported to irreversibly block transmission in a manner dependent on the extracellular calcium ion concentration. Jackson, H. et al. in *Excitatory Amino Acid Transmission*, pp. 51-54 (Alan R. Liss, Inc., New York 1987).

Bowers, C. W., et al., *PNAS (U.S.A.)* 84: 3506 (1987), report that a toxin isolated from *Hololena curta* appears to have a specific and direct effect on presynaptic calcium channels in neurons. The toxin is said to be a polypeptide composed of at least two disulphide-linked subunits of apparent molecular weights of 7000 and 9000 based on SDS-PAGE (sodium dodecyl sulfate electrophoresis). The authors hypothesize that this toxin acts by a potent and long-lasting inhibition of voltage-dependent presynaptic calcium channels and propose its use as a molecular probe for synaptic physiology.

Adams, M. E., et al, *Insect Neurochem. Neurophysiol.* (Pap. Int. Conf.) 2d, 397–400, 1986, report that they have isolated several toxins from *A.aperta* venom. One group of toxins are said to be polypeptides having an apparent molecular weight of 4800 daltons. Partial sequence information confirmed the polypeptide nature of these toxins and indicated strong homology among them. These toxins were not inactivated by boiling and three among them were resistant to trypsin. The authors stated that the presence of multiple cysteine residues within the sequences of these toxins raised the possibility that the structure of these toxins would have several disulphide bridges. Their activity is attributed to a presynaptic action on the sodium channel which was not reversed even after hours of washing.

Another smaller toxin (of molecular weight said to be less than 1000) isolated by the same investigators is said to be hydrophylic and to act postsynaptically because it was observed to cause a gradual diminution of the excitatory postsynaptic potential (EPSP) leading to its eventual block. However, this toxin is not otherwise characterized and the method for isolating it from *A.aperta* venom is not described. (In contrast, as will be shown below, the active factors of the present invention have a molecular weight of 300–500 daltons and act presynaptically.)

The authors of Adams et al, suora, also raised the possibility of using these toxins as pharmacological tools in the identification of chemicals affecting synaptic transmission.

Isolation and identification of calcium channels is of considerable interest because it would provide methods for regulating calcium ion transport through cell membranes (notably via use of appropriate blocking agents) which would have several research and diagnostic applications as well as therapeutic potential. Identification of such channels would also help increase the scientific understanding of membrane transport mechanisms.

Novel methods and factors for specifically and reversibly blocking calcium channels with high affinity would be useful, inter alia, in isolation and identification of calcium channels, in selective blocking of such channels (to avoid interference due to calcium channel-mediated responses with other membrane phenomena under study) and in drug screening and design.

OBJECTS OF THE INVENTION

Among the objects of the present invention are the following:

to isolate calcium channels;

to purify and characterize calcium channels;

to provide factors that bind calcium channels specifically;

to isolate and characterize such factors;

to provide a method for purifying calcium channels and/or for blocking voltage-dependent calcium conductance mediated by such channels;

to provide methods for regulating and/or for investigating the regulation of calcium transport through membranes;

to provide methods for identifying disorders in membrane transport;

to provide methods for investigating membrane transport of particles and entities including but not limited to calcium ions;

to provide methods for screening other agents or entities for their possible effect on cell membrane transport.

These and other objects of the invention will be apparent to those skilled in the art in light of the present specification, appended claims and accompanying drawings.

SUMMARY OF THE INVENTION

In one aspect, the invention is directed to calcium channel proteins responsible for HTCC in mammalian cell membranes, particularly in neuron membranes.

In another aspect, the invention is directed to non-polypeptide factors isolated from the venom of funnel-web spiders and capable of binding such calcium channels and blocking the voltage-dependent calcium conductance of cell membranes completely, specifically, with high affinity, but reversibly.

In still another aspect, the invention is directed to a method for purifying calcium channels by subjecting an impure preparation containing such channels to hydrophobic affinity chromatography using as the affinity adsorbent a calcium channel-blocking factor isolated from the venom of funnel-web spiders on a polysaccharide or monosaccharide support medium, thereby causing said channel to be retained in said affinity medium while excluding said impurities in the eluant; and recovering said channel from said medium in purified form.

In yet another aspect, the invention is directed to methods for regulating calcium ion transport across a cellular membrane comprising exposing said membrane to a calcium channel-blocking factor (which is not a polypeptide) isolated from funnel-web spider venom thereby causing said factor to bind specifically to, and block, said calcium channels.

BRIEF DESCRIPTION OF THE DRAWINGS

FIGS. 1 through 3 contain a series of tracings showing the effect of funnel-web spider venoms on voltage-dependent calcium conductance and action potential in Purkinje cells.

FIG. 4 shows the effect of *A.aperta* venom on the excitatory postsynaptic potential of a Purkinje cell.

FIG. 8 was obtained from computer manipulation of a recording of the type of FIG. 7.

FIG. 10 is a recording showing the opening of calcium channels and their blockage by *A.aperta* venom at various concentrations.

FIG. 16 is a probability that a reconstituted calcium channel be open (16A) or closed (16B) at a given potential value.

FIG. 17 is a plot of the mean duration of the open state of a reconstituted calcium channel.

FIG. 18 is a plot of current amplitude times the probability that the calcium channel of the present invention be open as a function of holding potential.

FIG. 19 is a plot of the relationship between current amplitude and holding potential for a reconstituted calcium channel according to the present invention.

DETAILED DESCRIPTION OF THE INVENTION

Figures 3A, 3B:
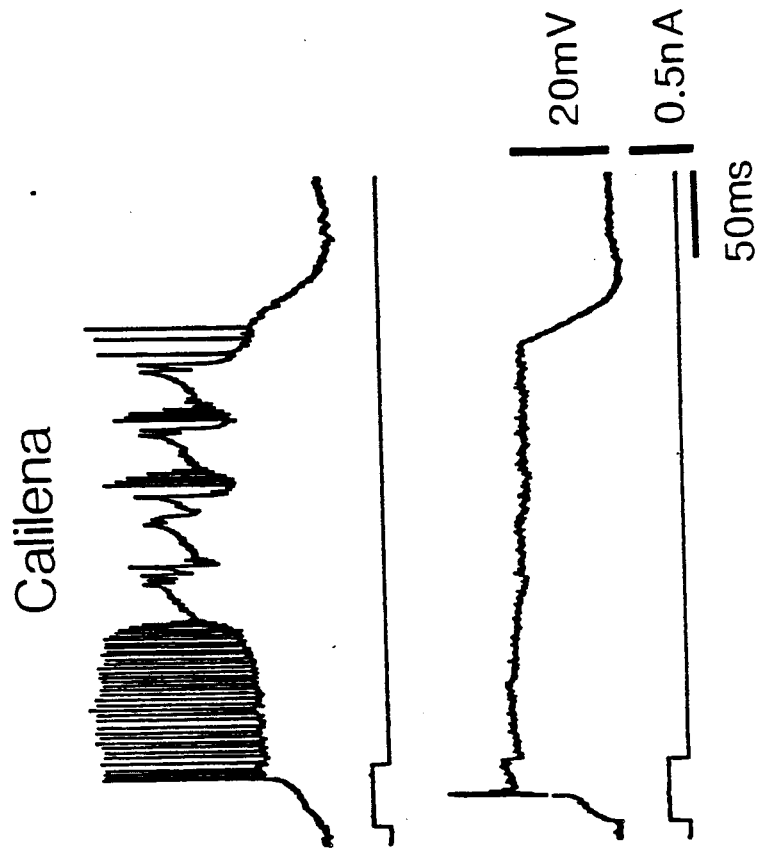

The calcium channels of the present invention are useful in assays and other procedures for testing the transport properties of cell membranes. Another use for these channels is in in vitro screening assays to screen compounds or other agents for their effect on membrane transport in both in vivo and in vitro systems. A further use of these channels is in regulating calcium transport through cell membranes by use of blocking agents that bind these channels and block their calcium ion-transporting activity.

For example, well-known methods may be used to raise polyclonal or monoclonal antibodies to the calcium channels of the present invention. Such antibodies may then be used in conjunction with standard immunofluorescence or radioimmunoassay techniques in assays for determining the extent to which disorders may result from abnormally high or abnormally low incidence or transport capacity of the calcium channel in selected cell membranes. Such antibodies may also be used as immunoaffinity adsorbents to further purify such calcium channels.

Screening procedures within the scope of the present invention include procedures for testing the ability of physical factors or chemical entities to affect calcium ion transport through, and both high- and low-threshold calcium conductances of, cell membranes. For example, the calcium channels of the present invention, reconstituted in a lipid bilayer, may be used to test the effect of environmental factors, as well as that of various compounds on voltage-dependent calcium conductance. Alternatively, the protein can be used to test the ability of novel or previously untested compounds to compete with known labelled calcium channel blocking agents for binding to the calcium channels. Such factors and entities may then be considered likely to affect calcium transport in vivo and would therefore constitute suitable candidates for further in vivo evaluation.

Use of such in vitro assay systems would not require use of large numbers of experimental animals. The methods to be employed in such screening assays are well-known to those skilled in the art.

The present inventors found that venoms from funnel-web spiders and active low-molecular weight factors isolated from such venoms reversibly bind to calcium channels with sufficient specificity and affinity to extinguish calcium, conductance in neurons and to permit isolation and purification of calcium channel structures.

Funnel-web spider venoms can be extracted from spiders according to techniques well-known in the art and are commercially available from C. Kristensen, Spider Pharm, Black Canyon City, Ariz. In addition, some of the *A.aperta* venom used in the present experiments was purchased from BioActives, Inc., Salt Lake City, Utah.

The active factor can be purified from each venom by column chromatography. These factors are highly charged and hydrophilic and have a molecular weight of less than 700 daltons (specifically, within the range of 300–500 daltons). The calcium-blocking activity was absent in acidified preparations containing the active factors of the present invention but was restored upon neutralization of the acid. The factors resist boiling and their activities are unaffected by sulfhydryl group-reducing agents, such as dithiothreitol. Their behavior on chromatography columns especially designed for protein purification and characterization and on isoelectrofocusing gels indicates that these factors are not polypeptides. (It is understood in this discussion that a "polypeptide" has a molecular weight of at least about 3000 daltons.) Their ability to be coupled to fluorescein and agarose gel indicates that NH groups are present in their structure.

As calcium channel blockers, these factors may be used, inter alia, in blocking calcium conductance of cell membranes and thus preventing interference from this conductance with measurements and monitoring of other conductances or transport properties of such membranes. In other words, because of the specificity and high affinity with which these factors block calcium channels they may be used in a manner analogous to that of tetrodotoxin (TTX) a well-known sodium channel blocking agent. These factors can also be used in preventing transmitter release resulting from the activation of the present high-threshold calcium channels and in associated drug design.

The active venom-derived factors of this invention can be coupled to a polysaccharide chromatographic support medium and used to purify calcium channel proteins by affinity chromatography.

In initial experiments, crude venoms were used in determining calcium channel blocking activity and in purifying the calcium channel. However, it is preferred to use a purified preparation, such as the active fraction(s) obtained from purification of venom by column chromatography preferably performed after boiling the venom.

The present inventors have demonstrated that even very small amounts of venom (or active factor derived from a partial chromatographic purification of funnel-web spider venom) are capable of blocking high-threshold calcium conductance spikes in vitro completely and with specificity, i.e., without affecting the rapid sodium conductances or the low-threshold, non-inactivating sodium conductances of the same cells.

In one type of experiment, direct somatic depolarization of Purkinje cells produced rapid, sodium-dependent, repetitive firing as well as oscillatory calcium-dependent spikes. After exposure to a bath containing venom (or active factor) the tetrodotoxin-sensitive, fast-action potentials were modified in that the normally large after hyperpolarization potential was reduced in amplitude as illustrated in the FIG. 1 inset which is a superimposition of the first spike in tracing A and the first spike in tracing C). In particular, dendritic, calcium-dependent, all-or-none responses were clearly blocked as recorded from both the somatic level (FIG. 2) and from direct dendritic impalement.

In another set of experiments, synaptic activation of the Purkinje cells via the climbing fiber afferents of inferior olivary cells produced an initial blockage of dendritic spikes and a simplification of the complex spike in the cells. However, the synaptic potential was not blocked. This indicates that the venoms (and active factors) do not substantially affect the calcium current which generates transmitter release from the climbing fiber. These results suggest that the calcium channels responsible for mediating dendritic calcium spikes may be different in some respect from those responsible for synaptic transmitter release. Similarly, experiments on the synaptic transmission in the squid giant synapse show that the active factor of the present invention prevents postsynaptic response by interfering with the inward calcium channel at the presynaptic terminals and, via this interference, preventing presynaptic transmitter release.

In addition, the active factors of the present invention have been shown to block high-threshold calcium conductances in thalamic, hippocampal and inferior olivary neurons. There is also reliable evidence that the channels recognized by these factors are not the same type of channels as those blocked by nifedipine ($5 \times 10^{-6}$M) or omega-conotoxin ($10^{-5}$M), since neither blocker had an effect on the calcium channels isolated in accordance with the present invention.

All funnel-web spider venoms and active factor isolates were highly active and specific in blocking calcium conductance. Blockage was complete within 10-15 minutes after exposure to the venom or active factor. The effect was reversible upon washing for at least about 30 minutes. Sodium conductance was unaffected. The threshold venom (or active factor) level for inducing blockage is expected to be dependent to a certain extent on the extracellular calcium concentration and on the applied current (or potential) and thus cannot be quantified except in those relative terms. In the experiments described here, a concentration of venom of $0.625 \times 10^{-3}$ microliters per ml of fluid surrounding the cell membrane was well above the threshold for an extracellular calcium ion concentration of 2mM and for currents ranging between about 0.15 and 2nA. The complete blockage of calcium entry by the active factor of the present invention was dramatically illustrated in a set of experiments using the fluorescent calcium indicator fura-2 intracellularly. Extracellular presence of the factor (at a concentration of about 10nM) completely inhibited the vivid intracellular fluorescence which otherwise accompanied calcium entry into a Purkinje cell (data not shown).

The active factors can be extracted from the venoms by chromatography, preferably using a polysaccharide medium capable of separating low molecular weight components. Since the active factors resist boiling (which causes a large portion of the other venom components, especially polypeptides, to precipitate) the purification is improved by loading onto the column the supernatant remaining after boiling of the venom components.

Other methods for purifying these factors without inactivating them are within the skill of the art in light of the present disclosure.

The active factors can be labelled by fluorescein (or another noninactivating, detectable label) and can be used to detect the location and frequency of calcium channels on preferably homogeneous cell preparations.

The calcium channels of the present invention can be purified by affinity chromatography, specifically hydrophobic affinity chromatography in which an active factor isolated from venom is used as the affinity adsorbent after being coupled (covalently bonded) to one of the well-known polysaccharide or monosaccharide support materials (usually gels) suitably modified. Gel preparation and coupling can be performed in accordance with the general procedures described in *Affinity Chromatography*, Scouten, W. H., John Wiley & Sons, 1981, pp. 45–49 and *Affinity Chromatography*, Dean, P. D. G., et al, Editors, IRL Press, 1985. The initial gel preparation is preferably performed in accordance with the manufacturer's instructions. A particularly suitable procedure for coupling affinity adsorbent materials to Sepharose ® gel represents a modification of that described by Caron, et al, *J. Biol. Chem.*, 254:2923-2927, 1979 and by Cherksey, et al, *J. Membr. Biol.*, 84:105-116, 1985 and can be used here, preferably with some further modifications as described below.

Suitable support materials include gels made from purified agarose (such as a Sepharose ® made by Pharmacia Fine Chemical Co., Piscataway, N.J.); alpha-linked dextran (such as Sephadex ® also made by Pharmacia); as well as cellulose and even short-chain polysaccharides and monosaccharides the, use of which for protein purification generally is well-known in the art.

A preferred gel material for use as a chromatographic support is Sepharose-4B (containing 4% agarose and permitting purification of proteins with a molecular weight within the range between $6 \times 10^4$ and $20 \times 10^6$ D). This material is first modified with a linker group, which will bind the calcium channel blocking factor without affecting its channel-binding ability, in order to facilitate bonding of the factor onto the support. An epoxide linker group, preferably a glycidyl ether such as butane diol diglycidyl ether, may be used for this purpose.

The factor is then coupled to the modified gel support. Coupling to the modified Sepharose 4B takes place preferably in the presence of a base, such as $NaCO_3$, and the resulting material (after washing) may be used for purification of the calcium channel.

It should be noted that many other methods for coupling an affinity adsorbent to a gel support are available in the art, and could have been used instead, the only proviso being that the ability of the support-bound adsorbent to bind the calcium channel should not be substantially affected.

Purification of these calcium channels may be accomplished by chromatography, e.g., by applying an impure cell membrane preparation to the active factor-modified gel, washing off the unbound material and then eluting the channel.

The thus purified channel indeed functioned as a calcium channel when reconstituted in a lipid bilayer as described in Miller, C., et al, *J. Membr. Biol.* 30:283-300, 1976, and Racker, E., et al, *Ann. N.Y. Acad. Sci.* 264:17-33, 1975 with such further details and modifications as described in Miller, C., Ed., *Ion Channel Reconstitution,* Plenum Press, New York 1986.

The channel was tested by applying potential across the bilayer while exposing the cis and trans chamber to various cationic solutions, symmetrical or not. The ability of the channel to transport both calcium and barium ions was thus confirmed. The channel was completely blocked by, $Cd^{++}$ and $Co^{++}$ which are known calcium channel blockers and by the active factor of e.g. *A.aperta* venom.

In experiments with native vesicles labelled with a calcium chelator label (such as quin-2, fura-2, indo-1, or acetoxymethyl esters thereof available from Molecular Probes, Plano, Texas) intravesicular fluorescence elicited by calcium uptake was blocked by the presence of venom in the surrounding medium, further indicating that the thus isolated structure is the same calcium channel which is subject to blockage by the untreated funnel-web spider venoms.

Nothing contained in this application should be interpreted as limiting the scope of the present invention to neurons. On the contrary, the invention is expected to be applicable to other types of calcium-channel bearing cells exhibiting HTCC and LTCC (including but not limited to heart muscle fibers and endocrine cells) the conductances of which are blocked by venoms and active factors thereof as described in this disclosure. Similarly, although the present invention is often illustrated by examples involving use of *A.aperta* venom, it encompasses factors having the same characteristics but isolated from other funnel web spiders.

All cited literature and patent applications are incorporated by reference.

The present invention is further described below by reference to specific examples intended to illustrate the invention without limiting its scope.

EXAMPLE 1

Demonstration of the Calcium Channel Blocking Activity of Venom from Funnel-Web Spiders and Chromatograohy Extracts Adult Hartley guinea pigs (400-600 grams from Camm Research Institute, Wayne, N.J.) were decapitated with a small animal guillotine under ether or sodium pentobarbital (Abbott Pharmaceuticals, Inc., N.Chicago, Ill., 40 mg/kg i.p.) anesthesia. A rapid craniotomy was performed to remove the squamous portion of the occipital bone, which allowed the total cerebellar mass, including the cerebellar nuclei, to be detached quickly with a metal spatula. The tissue was then immediately immersed in aerated Krebs-Ringer solution containing 124 mM NaCl; 55 mM KCl; 1.2 mM $KH_2PO_4$; 2.4 mM $CaCl_2$; 1.3 mM $MgSO_4$; $NaHCO_3$ (26 mM); and 10 mM glucose. This solution was kept refrigerated at 6° C. The cerebellar mass was then transacted sagitally and a single cell slice about 21 mm thick was isolated from the vermis or from one of the hemispheres. The slice was affixed with cyanoacrylate to the bottom of a plexiglass cutting chamber and agar blocks were used to surround the slice, thus providing side support. Once secured, the tissue was immersed in Krebs-Ringer solution at 6° C. and further sectioned with an Oxford G501 Vibratome (Ted Pella, Inc., Tustin, Calif.) to yield about six 200-(or in subsequent experiments 300) micron thick cerebellar slices, containing sagittal sections of all the cerebellar folia in a given rostrocaudal plane as well as central white matter and cerebellar nuclear cells. Following this procedure, the slices were incubated in oxygenated (95% $O_2$; 5% $CO_2$) Krebs-Ringer solution at 37° C. for about one hour.

After incubation, a slice was transferred to a recording dish such as that described in U.S. patent application Ser. No. 837,088 of Llinas, R. et al, filed Mar. 6, 1986 and also described in Llinas, R. et al, *J. Physiol.*, 305:171, 1980. The cerebellar slice was placed in a Sylgard plate (Corning Glass, Corning, N.Y.) at the bottom of a recording chamber and secured with a bipolar stimulating electrode pressing lightly on the white matter. The experiments were conducted at a chamber temperature of 37° C. maintained by a surrounding temperature-controlled water bath. The saline (Ringer's) solution used for continuous perfusion was also kept at 37° C. Tetrodotoxin ($10^{-6}M$) was used to block sodium conductance.

Various venom preparations were introduced in the chamber and the flow was turned off for various time periods as indicated below.

Purkinje cells were impaled with recording micropipettes under direct vision using Hoffman modulation microscopy (Hoffman, R., *J. Microsc.* 110:205-222, 1977). Intracellular recordings were obtained with micropipettes filled with 3M potassium acetate or 1M tetraethylammonium chloride (TEA) and having an average D.C. resistance of 60-80 megaohms. Synaptic activation of the cells was effected with a bipolar stimulation electrode located on the white matter at the basis of the folium studied. Direct stimulation of the Purkinje cells was implemented with a high-input impedance ($10^{12}$ Ohms) bridge amplifier.

In this series of experiments, $0.625 \times 10^{-3}$ microliters of venom were used (unless otherwise specified) per ml of extracellular medium. The small amount of venom used is indicative of the affinity of the active factor for calcium channels. (Minimum effective amounts can be easily determined by assay of serial dilutions of the venom or active factor.) Representative results of the experiments described below are illustrated in FIGS. 1-4.

FIG. 1 is a series of tracings A through D of intracellular recordings of Purkinje cells in vitro. Upon injection of an outward (depolarizing) current pulse, indicated by the lower trace, the neurons responded with firing having both sodium-dependent and calcium-dependent spikes (the latter being indicated in tracings A and B by arrows). Tracings A and B show the normal electrical response of the Purkinje cells in the absence of venom. Tracings C and D show the cell responses at 4 minutes (respectively) after introduction of *A.aperta* venom in the recording chamber medium (in each case).

Tracing C shows that a small depolarizing current (approximately 0.2nA) generates a burst of spikes (action potentials) and a plateau potential, the latter due to the non-inactivating ("persistent") sodium conductance; no calcium spikes are present and there is no calcium-dependent component to the plateau potential. In addition, the after hyperpolarization that follows each action potential in A is reduced in C and D (as illustrated in the inset). This reduction indicates that in addition to blocking the calcium conductance, the venom also affects the calcium-dependent potassium conductance, which is expected since calcium can no longer enter the cells and activate expulsion of potassium. By contrast, neither the transient nor the persistent sodium conductance is affected.

FIG. 2 shows a similar experiment but the sodium conductance was blocked with TTX (to ensure that sodium conductance would not contribute to the electrical response of the neuron) and the venom used was from the funnel-web spider *Hololena, curta*. In Tracing A, recorded in the absence of venom, a single current step generated a depolarization and a set of all-or-none calcium spikes. Tracings B through E were recorded respectively at 4, 6, 8 and 10 minutes following addition of *H.curta* venom and dramatically illustrate the effect of calcium conductance blockage by the toxic action of the venom over time. The blockage of calcium conductance, causes first the degeneration of the spikes (in B and C) and the appearance of a plateau potential (in B and C) followed by the gradual disappearance of the plateau potential (in D) until its extinction (in E).

FIG. 3 shows the results of a similar experiment using the venom of Calilena funnel-web spider. In response to an injection of a current for a short period of time, A (control without venom) shows a burst of spikes followed by a burst of calcium dependent action potentials (indicated by arrows). In B, recorded 6 minutes after the Calilena venom was introduced in the bath, only a (sodium-dependent) plateau potential is evoked indicating that the Calilena venom is specific to a voltage-dependent calcium channel and not to a voltage-dependent sodium channel.

The apparent absence of the sodium-dependent fast spikes that would be expected to follow the first such spike observed in tracing B is due to the substantially increased resistance of the cell (indicated by the large area defined by the sodium-dependent plateau potential) due to the blockage of calcium channels and the consequent preclusion of calcium ions from entering the cell and activating the exit from the cell of potassium ions.

FIG. 4 contains tracings of intracellular recordings from Purkinje cells following activation of climbing fiber afferents (from inferior olivary cells). The excitatory post-synaptic potential (EPSP) in A (control) is in the form of a normal spike. In B, 4 minutes after addition of *A.aperta* venom, repetitive action potentials are seen but without a calcium component. In C, the EPSP was measured in the presence (a) and absence (b) of an action potential. In D the response shown in C(b) was subtracted from that in C(a). The result is typical of a pure sodium conductance. This confirms that *A.aperta* venom is a specific calcium-conductance blocker and does not affect sodium conductance. However, the EPSP evoked after poisoning indicates that synaptic transmission still takes place at the concentration of *A.aperta* venom used. It is therefore postulated that the channel that generates calcium-dependent spikes may be more responsive to blockage from the venom (or more quickly accessible to the venom) than the calcium channel responsible for synaptic release in the climbing fiber system. However, after lapse of additional time from the introduction of the venom in the recording chamber medium, synaptic transmission is also blocked. A higher venom concentration will also cause blockage of the synaptic transmission.

Similar results were obtained when active factors isolated from venom were used instead of crude venom.

In yet another set of experiments, the sodium and potassium conductances were blocked with TTX ($10^{-6}$M) and TEA (tetraethylammonium chloride; $10^{-5}$M) and the blocking effect on the calcium spike was tested. When compared to results obtained using only the venom or the active factor from the venom (and no TTX nor TEA), it was confirmed that the active factor affects only the calcium conductance and not the sodium or (calcium-independent) potassium conductance.

EXAMPLE 2

Purification of Spider Venom

Figure 5:
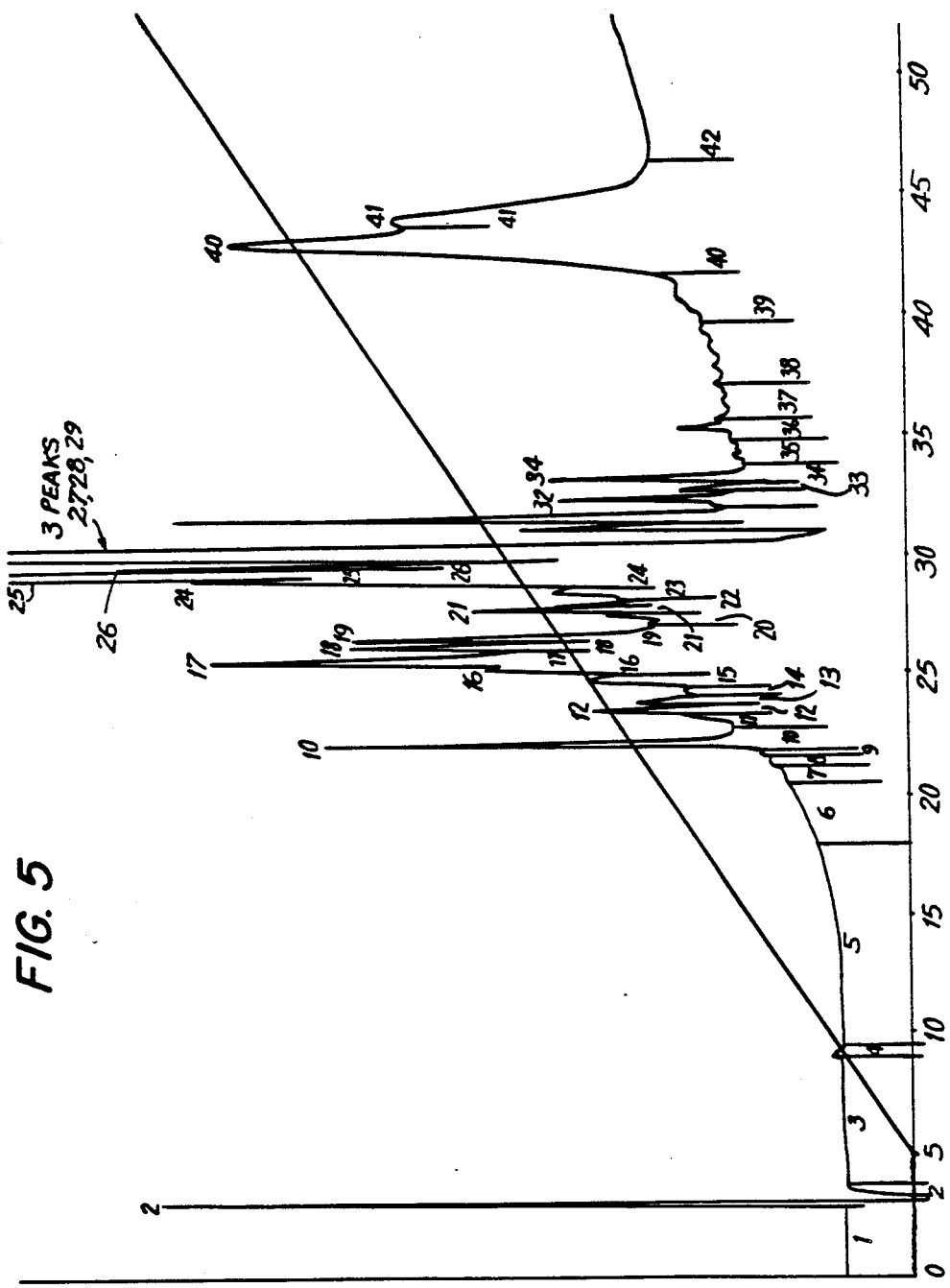
FIG. 5 is a high-pressure liquid chromatography elution profile of *A.aperta* venom.

Upon being subjected to High Pressure Liquid Chromatography (HPLC) on a C-3 hydrophobic affinity column using a phosphate gradient, 10 microliters of *A.aperta* venom yielded the elution profile shown in FIG. 5. The active fraction was fraction 40 as demonstrated by a calcium-conductance assay of the type described in Example 1.

Purification using a C-4 HPLC column, however, was not possible. This indicates that the ability to isolate an active fraction from the C-3 column was due to complexation of the active factor of the present invention with other components or contaminants.

Figure 6:
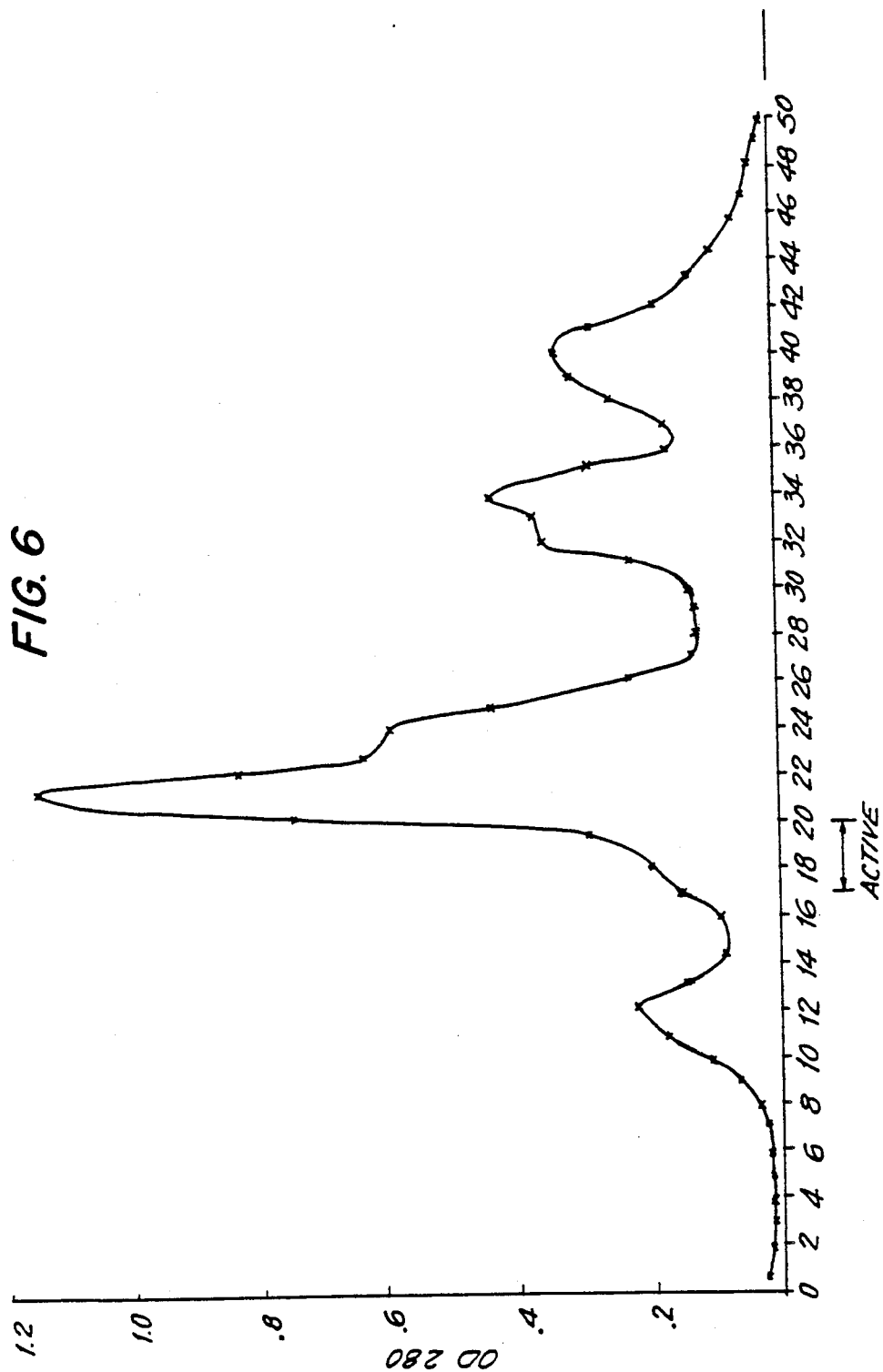
FIGS. 6 and 13 are Sephadex® G15 chromatographic elution profiles of *A.aperta* venom.

A preferred reliably reproducible chromatographic purification procedure was conducted on a Sephadex G-15 (alpha-linked dextran polysaccharide gel from Pharmacia, Piscataway, N.J. capable of separating components having a molecular weight of 1500 or less) as follows: Fifty microliters of *A.aperta* venom diluted 1:4 in saline buffer was first boiled for two minutes; the supernatant was separated by centrifugation at 3000×g for 10 minutes and was then subjected to chromatography in a Sephadex G-15 (1×25 cm) column using 0.5M NaCl as the buffer. Fifty 1-ml fractions were collected. The active fractions were 17 through 20 (corresponding to an apparent molecular weight range of 300–500 daltons) as confirmed by calcium channel blockage of the type described in Example 1. The elution profile of this chromatographic purification by optical density measurement at 280 nm is shown in FIG. 6.

Figure 13:
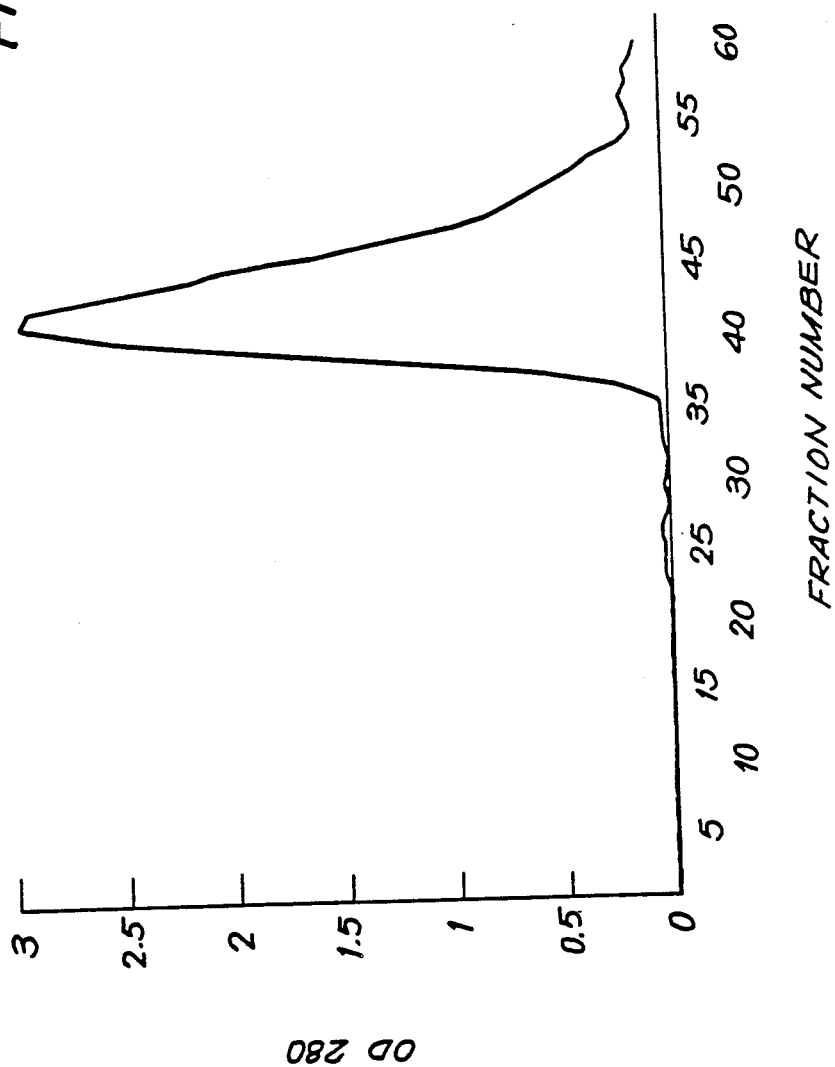

The procedure was repeated but 0.5 ml fractions were collected. The results are shown in FIG. 13. The active fractions were fractions 30–35 indicated by the arrows. The large peak observed in FIG. 13 was totally devoid of calcium-channel blocking activity and probably represents protein degradation products from boiling. The procedure was repeated with *Hololena curta* and Calilena venom. The results, including the molecular weight range, were the same as for *A.aoerta*. The activity of all purified fractions was assessed electrophysiologically in accordance with the procedure of Example 1 on cerebellar slices from guinea pigs and on squid stellate ganglia as described in Example 14 below.

EXAMPLE 3

Labelling of Active Chromatographic Fractions

Twenty-five microliters of *A.aperta* spider milk (no dilution) were mixed with 0.1mg fluorescein isothiocyanate in 0.1M sodium borate (pH 9.3) and allowed to react for three hours at room temperature in the dark. The reaction mixture was subjected to column chromatography on a Sephadex G-10 column (which separates components with a maximum apparent molecular weight of 700 daltons) of 1×25 cm size using isotonic saline. Sixty 1-ml fractions were collected with the Cahu ++ channel-blocking activity being present in fractions 12-17. The exclusion volume was collected through fraction 9. The apparent molecular weight of the labelled material in the active fractions was less than about 700 daltons with about 400 attributable to the label.

On $Ca^{++}$ channel-blocking assay, the fluorescein-labelled active fractions demonstrated an ability to block the calcium channel.

EXAMPLE 4

Acid-Inactivation of Spider Venom

Ten microliters of 1:4 dilution of *A.aperta* venom to which acetic acid was added to a concentration of 0.1% did not block calcium conductance, but the blocking activity was restored on neutralization of the acid.

EXAMPLE 5

Reduction with Dithiothreitol

Ten microliters of *A.aperta* venom were mixed with ten microliters of 2% dithiothreitol (DTT). After 24 hours, samples of the venom subjected to these reducing conditions were assayed for calcium blockage and found to have activity similar to that of the venom prior to its exposure to DTT. Therefore, it does not appear that disulfide bonds are involved in the activity of this venom.

The DTT test was repeated using 5% DTT in the supernatant from the centrifugation of *A.aperta* venom after boiling the venom for 10 min. The boiling procedure was then repeated. Electrophysiologically tested calcium blocking activity remained the same after boiling and DTT treatment.

EXAMPLE 6

Coupling of Venom to Polysaccharide Affinity Medium

*A.aperta* venom was covalently bonded to Sepharose 4B as follows.

Fifty ml Sepharose 4B gel were mixed in 300 ml water containing 0.3M NaOH. The mixture was stirred. 25 ml of 1,4 - butane diol diglycidyl ether were added drop-wise and the mixture was stirred gently overnight at room temperature. The gel was washed with four liters of water. (Upon addition of sodium azide and refrigeration, the thus prepared gel can be stored for one week.)

After washing, 25 ml of the ether-coupled gel were suspended in 100 ml of 0.2M $NaCO_3$ buffer, pH 11. Approximately 50 microliters of the *A.aperta* venom were added and stirred overnight in a cold room. The gel-coupled venom components were washed with three liters of water containing 1M NaCl followed by a wash with one liter of water. 100 ml of 0.2M $NaCO_3$ buffer, pH 11, were added and the mixture was stored in the refrigerator for one week. It was then washed with 3 liters of 1M NaCl and then with 4l of water and stored in water containing 0.1% sodium azide. This coupling protocol is preferably used with chromatography-purified active fraction of preboiled spider venom and has been used with fraction 40 and with the G-15-purified venom from Example 2.

The foregoing procedure was repeated to couple 100 microliters of active factor from *A.aperta* venom (purified in accordance with the preferred procedure of Example 2) to ether-coupled Sepharose 4B gel. The resulting affinity gel was used in purification of all cerebellar and squid obtic lobe preparations described in Examples 15 and 17 below.

EXAMPLE 7

Preparation of Guinea Pig Cell Membranes

Whole guinea pig brain (approximately 10 g) excised as described in Example 1 was homogenized into 400 mM sucrose, 5 mM Tris-HCl, pH 7.4, 0.1% PMSF (phenylmethylsulfonylfluoride), 0.1% bacitracin, 5 mM EDTA and approximately 2 units of Aprotinin protease inhibitor (Sigma). It was then subjected to differential centrifugation at 700×g for 10 minutes. The supernatant was recovered and subjected to further centrifugation at 12,000×g for 15 minutes using a Sorvall rotor apparatus (E. I. Dupont de Nemours & Co., Wilmington, Del.).

The supernatant was again subjected to Sorvall centrifugation at 47,000×g for 30 minutes. The pellet was saved. A small portion of the pellet (approximately 20 mg) was re-homogenized into 400 mM sucrose for native vesicles (see Example 11).

The remainder of the pellet was resuspended into 100 mM sodium citrate buffer pH 7.4 and 3% sodium choleate based on the total solution volume was added. The solution contained about 20 mg of membrane protein preparation per ml. The solution was stirred overnight in a cold room, was centrifuged at 47,000×g for 30 minutes and the supernatant was subjected to affinity chromatography in accordance with Example 8.

Preferably, guinea-pig cerebellar homogenate was used obtained as described in Example 1. Four or more cerebella were combined and the procedure described above in this Example 7 was repeated (10 volumes of the sucrose solution, ice-cold were employed for homogenization) and a Dounce homogenizer (Wheaton Scientific, Millville, N.J.) was used to homogenize and to resuspend the cerebellar material.

EXAMPLE 8

Purification of Calcium Channel Protein

The solubilized whole-brain product of Example 7 was applied to the venom-coupled gel of Example 6 (or to a gel linked with the active fraction(s) of a chromatographic extract of venom) and was stirred overnight at 4° C.

The gel mixture was washed with 10 volumes sodium citrate (100 mM; pH 7.4) containing 0.5% sodium choleate and vacuum-filtered. To remove the bound protein, the gel was resuspended into 20 ml of 1M $CaCl_2$ (pH 7.0) and 3% sodium choleate and stirred in a cold room for two hours. The preparation was vacuum-filtered and the filtrate was collected. The gel was again resuspended in the $CaCl_2$/choleate solution and the elution procedure was repeated.

The filtrates were pooled and dialyzed for at least 24 hours against 100 mM sodium citrate (pH 7.4) to remove the choleate. The dialyzate was concentrated against polyethylene glycol (MW 35,000), 2 ml of purified product were applied to a Sephadex G-25 column (1×25 cm) and the void volume was collected.

The thus purified protein was reconstituted into lipid vesicles using a 4:1 mixture of phosphatidylethanolamine/ phosphatidylcholine (PE/PC) in 400 mM sucrose formed by sonication and dialysis as described by Racker et al., supra.

The vesicles were applied to a Sephadex G-25 column (1×35 cm) and were collected in the void volume. In one set of subsequent experiments, they were fused with a planar lipid bilayer described by Miller, C. et al., J. Membr. Biol., 30:283-300 (1976) PE/PC =1:10 of 0.2 mm diameter. The rear (trans) chamber, was held at virtual ground. Potential was applied with a Ag/AgCl electrode and the vesicles were added to the front (cis) chamber. The solutions in each chamber could be changed independently in the course of the calcium channel confirmation experiments described below.

The solubilized cerebellar product of Example 7 was reacted batch-wise with 20 ml of the active factor-coupled gel (prepared in accordance with Example 6) as described above in this Example 7. The gel was separated from the solution by vacuum filtration and the gel cake was resuspended into 20 ml of 1M $CaCl_2$ (pH 7.0), 1% sodium choleate 10 mM HEPES (ph 7.4) and stirred at 4° C. for two hours. The preparation was filtered, the filtrate retained and the suspension/filtration procedure was repeated. The pooled filtrates were dialyzed and concentrated as described above and the protein-containing concentrate was desalted on a 1×25 cm Sephadex G-25 column equilibrated with 100 mM HEPES, pH 7.4. The void volume was collected and brought to 3% choleate.

The choleate-containing eluate was added to a 20ml cake of amiloride-Sepharose gel (prepared as described in Example 12, below) and stirred overnight at 4° C. The mixture was vacuum-filtered and the filtrate was again concentrated against polyethylene glycol (mw 35,000), desalted on Sephadex G-25 and extensively dialyzed against 400 mM sucrose, 10 mM HEPES, pH 7.4.

At each step of the procedure, samples were used to determine protein contact which was done by the Bradford assay (Biorad Laboratories, Richmond, Calif.). The overall yield was less than 0.0005%, a figure consistent with those of other membrane protein purifications.

Vesicles were then formed as described above.

Vesicles used for fluorescence studies were preloaded with the calcium-sensitive dye quin-2 by forming the vesicles on a 1×25cm Sephadex G-50 column equilibrated with 150 mM KCl/10 mM HEPES (pH 7.4) in the presence of the dye at a dilution of 20 microliters of a 50 mM stock solution per ml of protein solution.

The functional activity of the purified cerebellar protein preparation was studied using both the planar lipid bilayer technique described above and the "tip-dip" technique; Coronado and Latorre, *Biophys. J.* 43:231-236, 1983).

For the planar bilayer technique, a 25 mg/ml solution of PC in decane was painted across a 0.2 mm aperture in a plastic cup to form the barrier between two aqueous solutions. A single op-amp with a one-gigaohm feedback resistor was used as the current-voltage converter.

Bilayers were also formed on two-pull micropipettes with opening diameters of approximately one micron using a 3:1 mixture of PC/PE. Voltage was applied via the micropipette using a Dagan 8900 patch/whole-cell clamp (Dagan Corporation, Minneapolis, Minn.) with a 10-gigaohm head-stage. The bathing solution was held at ground.

Data obtained in the channel studies using channel protein preparations of cerebellar origin were amplified to 100 mV/pA and the membrane current was recorded on an HP3960 FM instrumentation recorder (Hewlett Packard Co., Palo Alto, Calif.) for subsequent analysis Data were filtered at lkHz and digitized at a sampling interval of 200 microseconds. The digitized records were then analyzed with a computer to obtain amplitude, open-time and closed-time distribution, (see FIGS. 14-20 and Example 13, below.)

EXAMPLE 9

Confirmation of $Ca^{++}$ Channel Activity

In this type of experiment, the chamber solutions initially contained symmetrical 0.5M sodium citrate solution and 5 mM TrisHCl. Potentials were applied as described by Miller, C. et al. *J. Membr. Biol.* 30:283-300 (1976). The equipment used was a simplified version of that described in Miller, C., Ed., *Ion Channel Reconstruction* Plenum Press (New York 1986) pp. 115 et seq.

Figure 7:
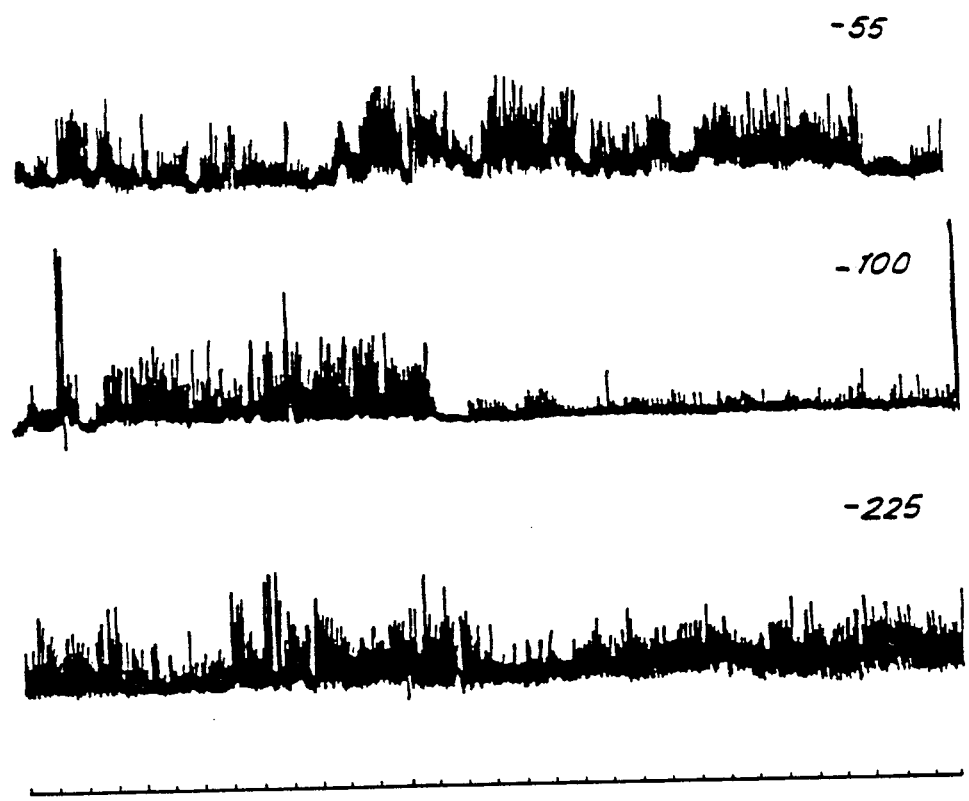
FIGS. 7 and 14 are recordings of ionic current due to the opening of a calcium channel contained in a reconstituted lipid bilayer at various holding potentials.
Figure 8:
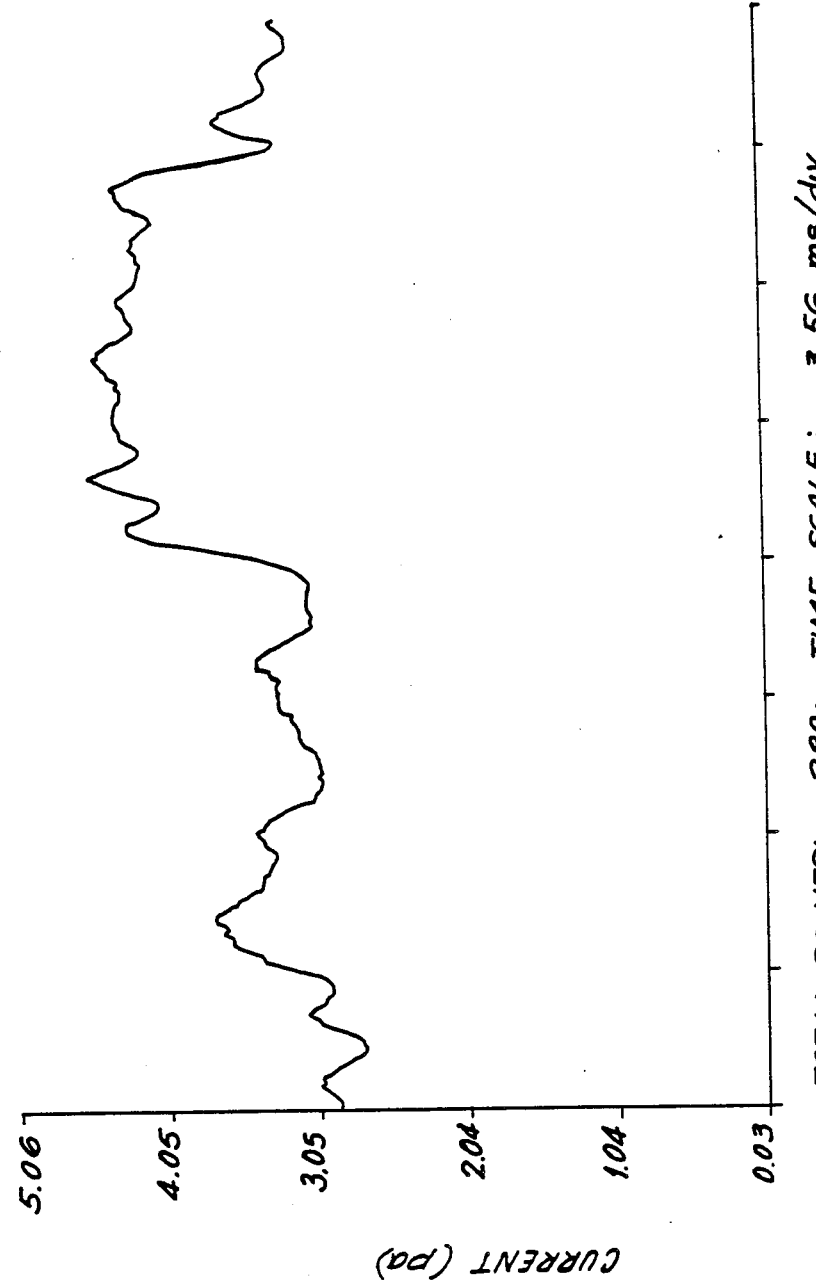
FIG. 8 shows the variation in amplitude of current due to the opening of a calcium channel as a function of time.

A symmetrical solution containing 100 mM $CaCl_2$, pH 7.5, was then used. A channel was observed at a conductance of approximately 10 pS as illustrated in FIG. 7 which was recorded in a similar experiment. Recordings were made on a chart moving at 5mm/min and having a sensitivity of 100 mV/chart vertical division (0.8mm). The opening of channels is evidenced by successive jumps in current (measured in picoamperes with lpA equal, to a vertical distance for 400 mV on the chart) indicated by the arrows on FIG. 7. A computer analysis of another similar recording yielded the graph of FIG. 8 wherein the opened channel is observed between the fourth and seventh divisions of the abscissa, Calcium channel activity was blocked by cobalt offering further confirmation that the purified protein was indeed the calcium channel of the present invention.

Figure 9:
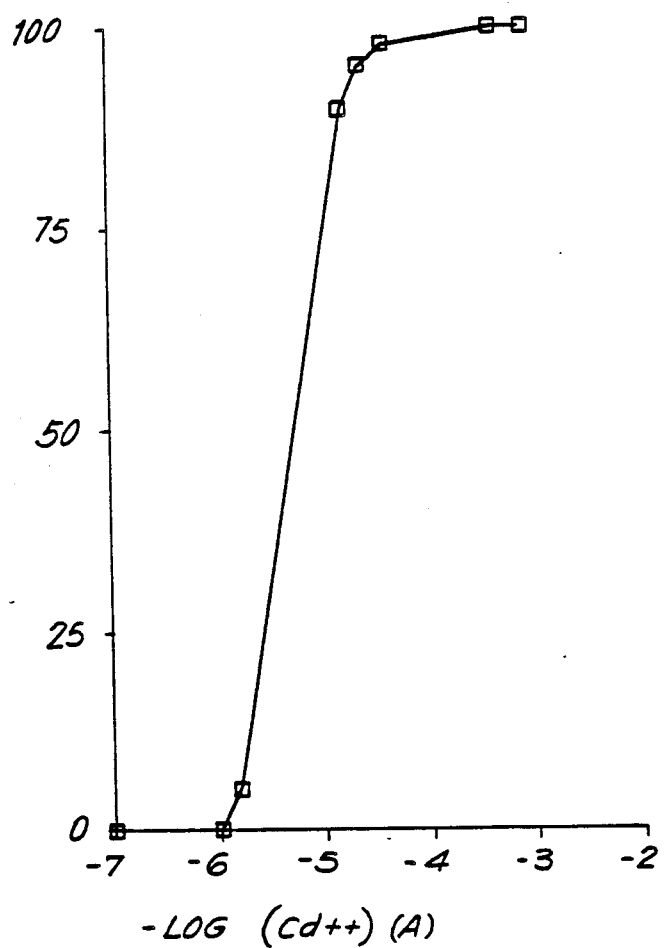
FIG. 9 is a graph showing the inhibition of the ionic current due to calcium influx as a function of the concentration of cadmium in the solution surrounding a vesicle incorporating calcium channels.

The calcium channel activity was also blocked by cadmium. FIG. 9 is the result of computer analysis of recordings such as FIG. 7 based on experiments involving use of cadmium as a calcium channel blocker. FIG. 9 shows how the current (measured by the average amplitude of signals such as those of FIG. 7) due to the calcium channel is inhibited by varying concentrations of Cd. The applied voltage ranged between +200 and −200 mV (based on the resting membrane potential) and was varied at 25 mV increments.

To obtain an amplification of the calcium channel response, $BaCl_2$ solution at 100 mM was substituted symmetrically in the bilayer chambers. A channel with a slope conductance of 15 pS was observed when the same voltage range (±200 mV) was used.

A summary of solutions and conditions used to test the lipid bilayer for calcium channel activity in the experiments described in this Example is given in Table II below:

TABLE II

| Solute | pH | Symmetrical | Voltage Range | Calcium Conductance |
|---|---|---|---|---|
| 1. 0.5 M Na citrate | 7.4 | Yes | ±200 mV | none |

TABLE II-continued

| Solute | pH | Symmetrical | Voltage Range | Calcium Conductance |
|---|---|---|---|---|
| and 5 mM Tris-HCl | | | | (control) |
| 2. 100 mM CaCl$_2$ | 7.5 | Yes | ±200 | 10 pS |
| 3. 100 mM BaCl$_2$ | | Yes | ±200 | 15 pS |
| 4. 100 mM CaCl$_2$ and 20 M × 10$^{-6}$ Co$^{++}$ | 7.5 | No outside only | ±200 | none |

EXAMPLE 1

Purification of Ca$^{++}$ Channel on Gel Bearing Purified *A.aperta* Venom

The active fraction shown in FIG. 5 (Fraction 40) and referred to in Example 2 was bound to Sepharose 4B as described in Example 6. Brain material was purified as described in Example 8. When reconstituted in a lipid bilayer, it displayed calcium channel properties as described in Example 9.

Addition of five microliters of *A.aperta* venom (1:4 dilution) extinguished the calcium channel activity when CaCl$_2$ symmetrical solution was used in the bilayer. The same results were obtained when using G-15-purified factor and crude venom as the affinity adsorbent.

FIG. 10 is a series of recordings of a lipid bilayer containing 250 mM symmetrical BaCl$_2$ solutions. The top recording represents bilayer behavior with occasional Ca$^{++}$ channels opening at a holding potential of −50 mV. The second is a recording from the same bilayer at −90 mV. Clear calcium channels were observed opening frequently (the recording speed was 25mm/sec). The remaining recordings show bilayer behavior after addition of various concentrations of *A.aperta* venom (1:100 dilution) at concentrations of 50, 100 and 200 microliters, at a holding potential of −90 mV. At 50 microliters, a "fast flicker" activity is induced which indicates that the channel is blocked at or near the dissociation constant between the blocking factor contained in the venom and the channel structure. At 100 and 200 microliter concentration, channel activity is completely blocked.

The preferred method of purifying the channel employs the active fractions from the G-15 Sephadex chromatography described in Example 2. The results of an experiment identical to this Example 10 are the same when the G-15-purified fraction was used.

EXAMPLE 11

Calcium Blockage Using Native Vesicles

The fraction-40 purified protein material saved for vesicle preparation from Example 7 (containing approximately 20 mg protein) was mixed with approximately 400 mg of phosphatidylethanolamine/-phosphatidylcholine (PE/PC =4/1) and 200 microliters of a solution containing 10 mgs of quin-2 (a fluorescent calcium chelator having the formula (2-[2-[bis(carboxymethyl) amino-5-methylphenoxy]-methyl]6-methoxy-8-bis(carboxymethyl) aminoquinoline available from Lancaster Synthesis, Eastgate England) in 2 ml of ethanol/water (approximately 1:40) isotonic saline solution. The mixture was sonicated and subjected to column chromatography using a G-25 column (a G-50 column could also have been used) and isotonic saline. The vesicles were collected in the exclusion volume, diluted with saline containing 100 mM KCl and 10$^{-7}$M valinomycin (an ionophore rendering the membrane permeable to K$^+$ ions available from Sigma Chemical Co, St. Louis, Mo.).

Figure 11:
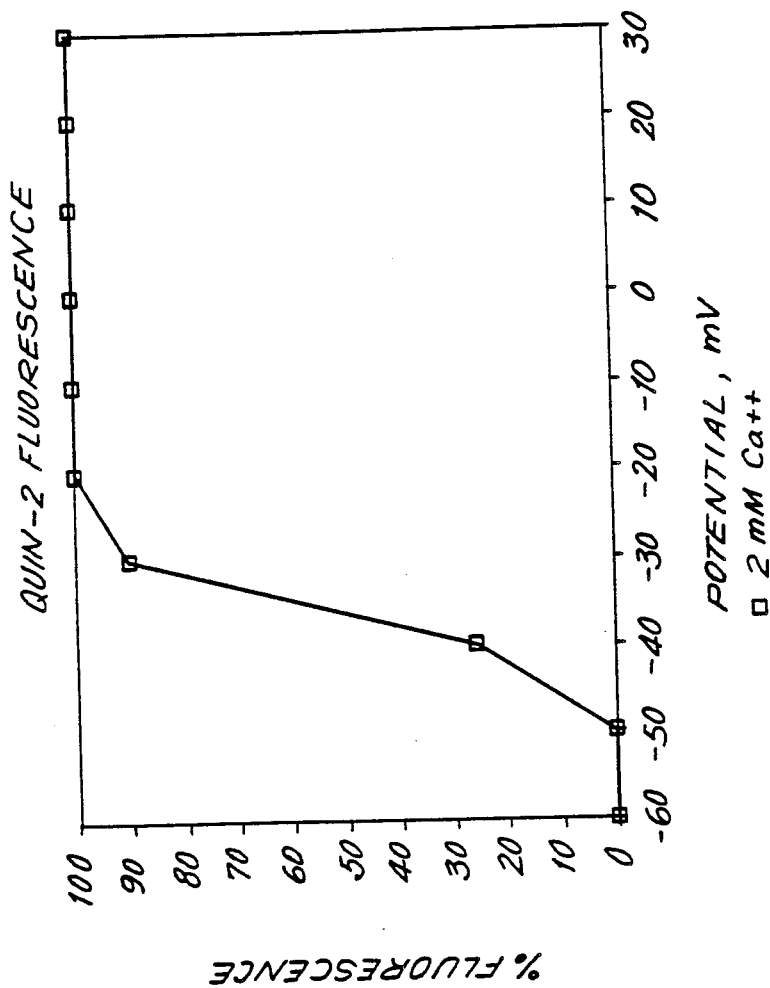
FIGS. 11 and 22 are graphs showing the increase in intravesicular fluorescence upon the opening of the calcium channel as a function of the difference in potential between the vesicle interior and the surrounding medium due to a differential in potassium ion concentration.

The vesicles (now containing 100 mM KCl) were then immersed in a 10 mM KCl solution. CaCl$_2$ (2 mM) was added to the surrounding solution with and without the previous addition of *A.aperta* venom. The differential in KCl concentration as between the interior of the vesicles and the surrounding solution creates a difference in potential which can be approximated using the Nernst equation for potassium. When this chemical potential reaches the threshold of the calcium channel, the calcium channel opens allowing Ca$^{++}$ from the surrounding solution to flow in the vesicle and chelate with the quin-2, resulting in measurable fluorescence. The results of such an experiment are shown in FIG. 11. When *A.aperta* venom (5 microliters, 1:10 dilution) was introduced to the surrounding solution prior to addition of CaCl$_2$, no substantial fluorescence could be measured inside the vesicle (data not shown).

Figure 12:
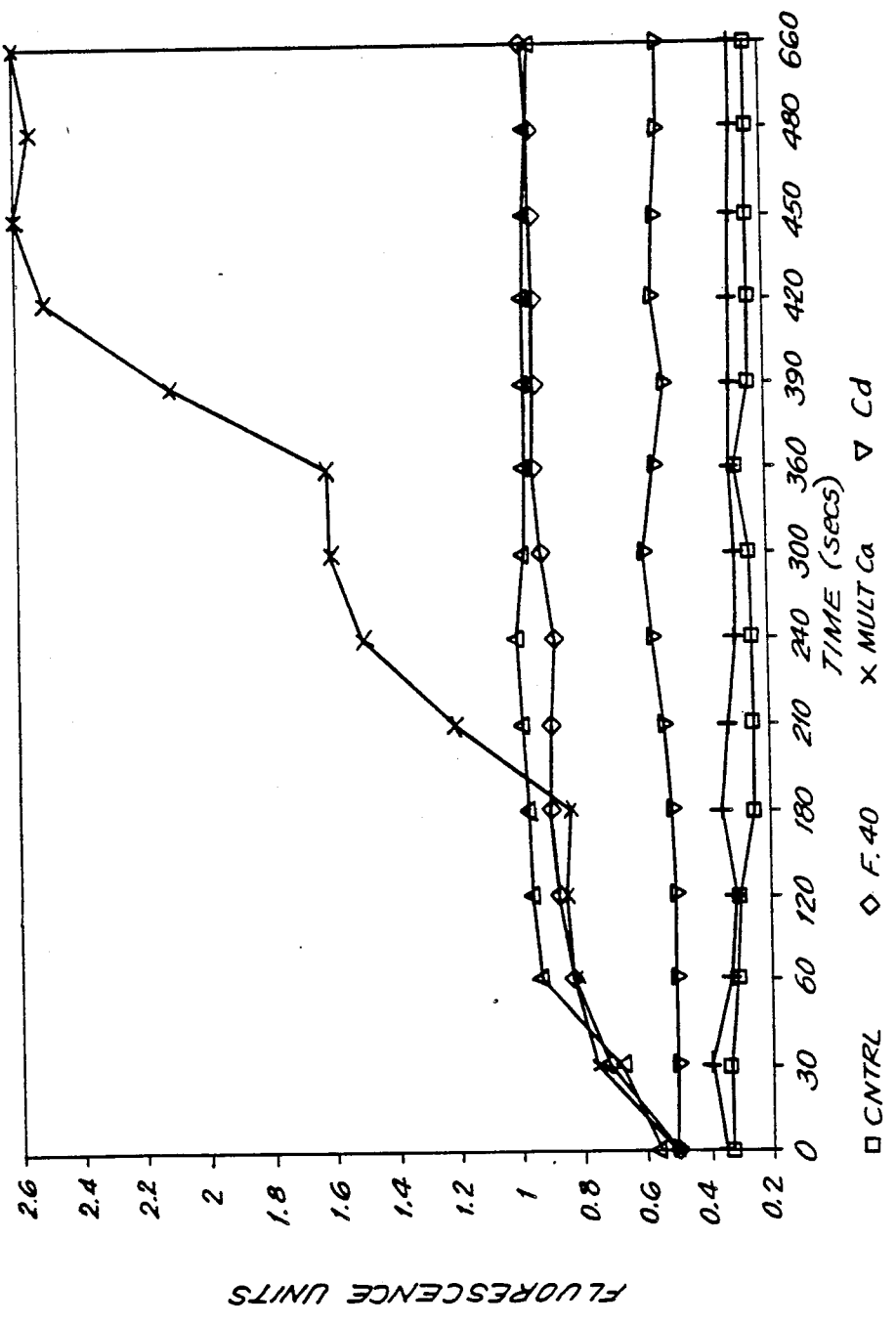
FIGS. 12 and 20 are graphs of the intravesicular fluorescence (as a function of time) observed upon introduction of calcium chloride in the solution surrounding a vesicle both in the presence and the absence of a calcium blocker.

In another experiment, the results of which are shown in FIG. 12, vesicles containing purified protein and vesicles not containing protein were simply exposed to 2 mM CaCl$_2$ (these vesicles did not contain KCl nor were exposed to valinomycin) in the surrounding solution. Fluorescence within the vesicles was then detected.

In FIG. 12, fluorescence measurements over time were taken for vesicles not containing protein (represented by open squares and crosses) vesicles containing protein (represented by upright triangles and diamonds) and for multiple additions of 2 mM CaCl$_2$ (represented by X's). The observed increase in fluorescence thus showed a clear dependence on the extravesicular calcium concentration. Upon addition of cadmium (100 micromolar) prior to addition of CaCl$_2$, the observed fluorescence (represented by inverted triangles) did not increase with time and remained at the baseline. (Fluorescence measurements are expressed in percent based on a 2 mM CaCl$_2$ standard.) The results of the experiments described in this Example 11 are fully expected to be the same when vesicles made with protein isolated with G-15-purified factor as the affinity adsorbent are used.

EXAMPLE 12

Preparation of Amiloride Gel

The drug amiloride specifically blocks the low-threshold calcium channel in central neurons (Tang C-M., et al., *Science*, 240:213, April 8, 1988). Amiloride (3,5-diamino-N-(aminoiminomethyl)-6-chloropyrazine carboxamide available commercially from Sigma Chemical Co., St. Louis, Mo.) can therefore be used to extract the low-threshold calcium channel from brain or cellular homogenate protein preparations such as those of Example 8.

An affinity gel was constructed from amiloride and

Sepharose using ethylene glycol as a coupling agent, as follows:

The ethylene glycol was covalently bonded to a purified agarose (Sepharose) support by washing 100ml of Sepharose CL4B beads with water, removing interstitial water by suction filtration, and adding to 80ml of water. NH4Cl was added to this suspension to a concentration of about 1M. The pH was raised to about 9. The glycol (50 ml/100 ml of Sepharose) was added slowly while the pH was maintained constant at 9 with NaOH and reaction was allowed to continue until the pH remained constant without further addition of NaOH. (This procedure is an alternative to the well-known cyanogen bromide coupling reaction and has the same general applicability as that reaction.)

Amiloride (1g) was added and the mixture was stirred overnight, filtered, and washed with water. The mixture was then brought to a pH of 4.5 and reduced with sodium borohydride at 4° C. for 12 hours. The resulting gel was washed and dried by vacuum filtration. Twenty milliliters of this gel were used in the purification of the cerebellar-origin material described in Example 9.

The drug amiloride specifically blocks the low-threshold calcium channel in central neurons (Tang C-M., et al., Science, 240:213, April 8, 1988). Amiloride (3,5-diamino-N-(aminoiminome- thyl)-6-chloropyrazine carboxamide available commercially from Sigma Chemical Co., St. Louis, Mo.) can therefore be used to extract the low-threshold calcium channel from brain or cellular homogenate protein preparations such as those of Example 8.

An affinity gel was constructed from amiloride and Sepharose using ethylene glycol as a coupling agent, as follows:

The ethylene glycol was covalently bonded to a purified agarose (Sepharose) support by washing 100ml of Sepharose CL4B beads with water, removing interstitial water by suction filtration, and adding to 80ml of water. NH4Cl was added to this suspension to a concentration of about 1M. The pH was raised to about 9. The glycol (50 ml/100 ml of Sepharose) was added slowly while the pH was maintained constant at 9 with NaOH and reaction was allowed to continue until the pH remained constant without further addition of NaOH. (This procedure is an alternative to the well-known cyanogen bromide coupling reaction and has the same general applicability as that reaction.)

Amiloride (1 g) was added and the mixture was stirred overnight, filtered, and washed with water. The mixture was then brought to a pH of 4.5 and reduced with sodium borohydride at 4° C. for 12 hours. The resulting gel was washed and dried by vacuum filtration. Twenty milliliters of this gel were used in the purification of the cerebellar-origin material described in Example 9.

EXAMPLE 13

Further Single-Channel Studies (A) Lipid Bilayers

Using both the planar and "tip-dip" lipid bilayer techniques, the electrical activity of cerebellar-origin calcium-channel preparations purified in accordance with Example 9 was measured in asymmetric solutions containing 80 mM $BaCl_2$, 10 mM HEPES (pH 7.4) on the cis side; 120 mM CsCl, 1 mM $MgCl_2$, 10 mM HEPES (pH 7.4) on the trans side (or in the patch pipette). When vesicles containing the purified protein were added, a jump in the conductance was detected typically within 10 mins. Single-channel recordings using barium-ion-containing solutions were difficult to obtain because of the fusion-promoting effect on this cation. This however does not affect the validity of the conclusions drawn from these experiments.

Figure 14A:
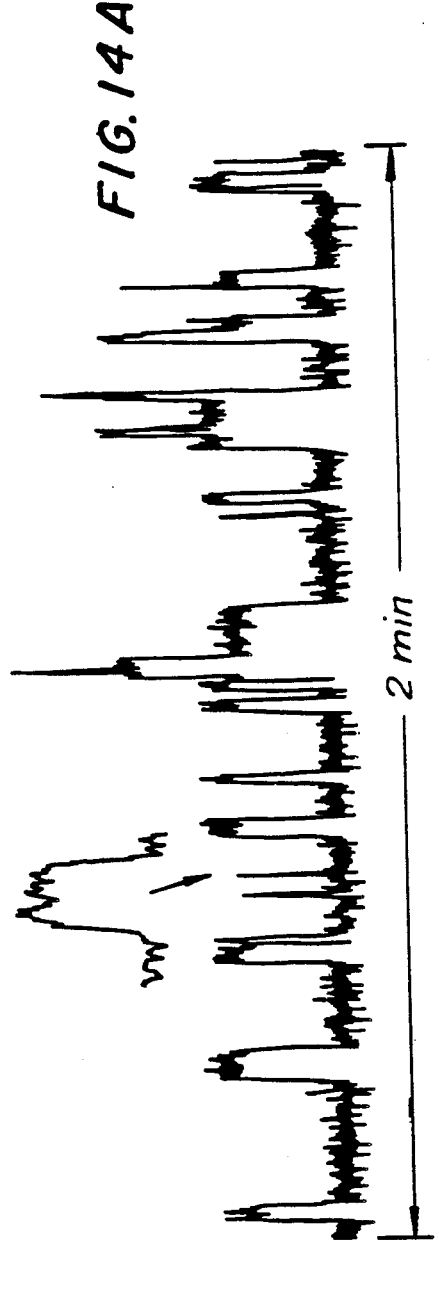

A typical recording is shown in FIG. 14A which is a two-minute tracing obtained at a potential of −40 mV (1picoampere corresponds to 18 mm). In this particular experiment, three channels (marked 1, 2 and 3) with identical conductances had fused with the bilayer, as evidenced from the amplitude distribution shown in FIG. 15. (The unmarked histogram corresponds to the baseline.) As can be seen in FIG. 14A, at this potential, there is a predominance of channel openings of long duration (i.e. greater than 1 second). Also present are rapid openings with durations of less than 100 milliseconds (see FIG. 14A inset which corresponds to the spike marked by the arrow).

Figure 14B:
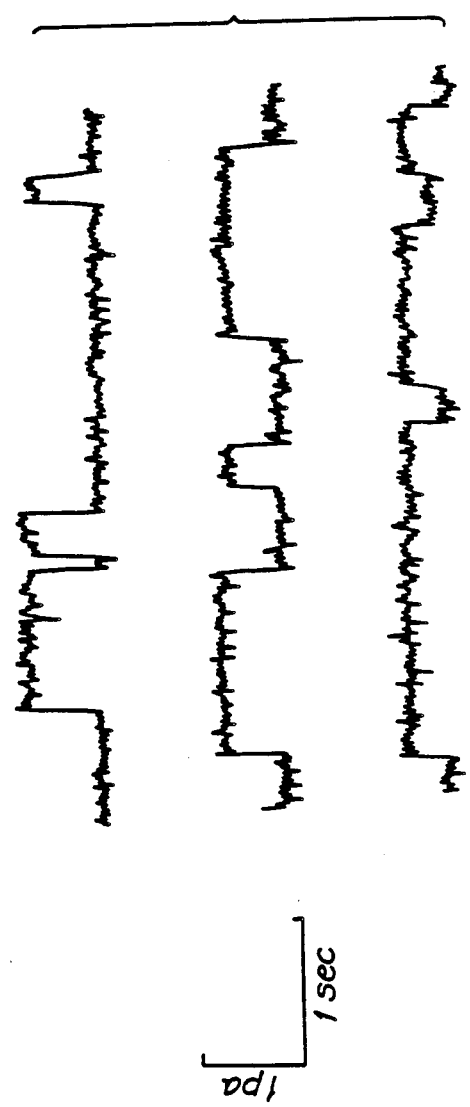
Figure 15:
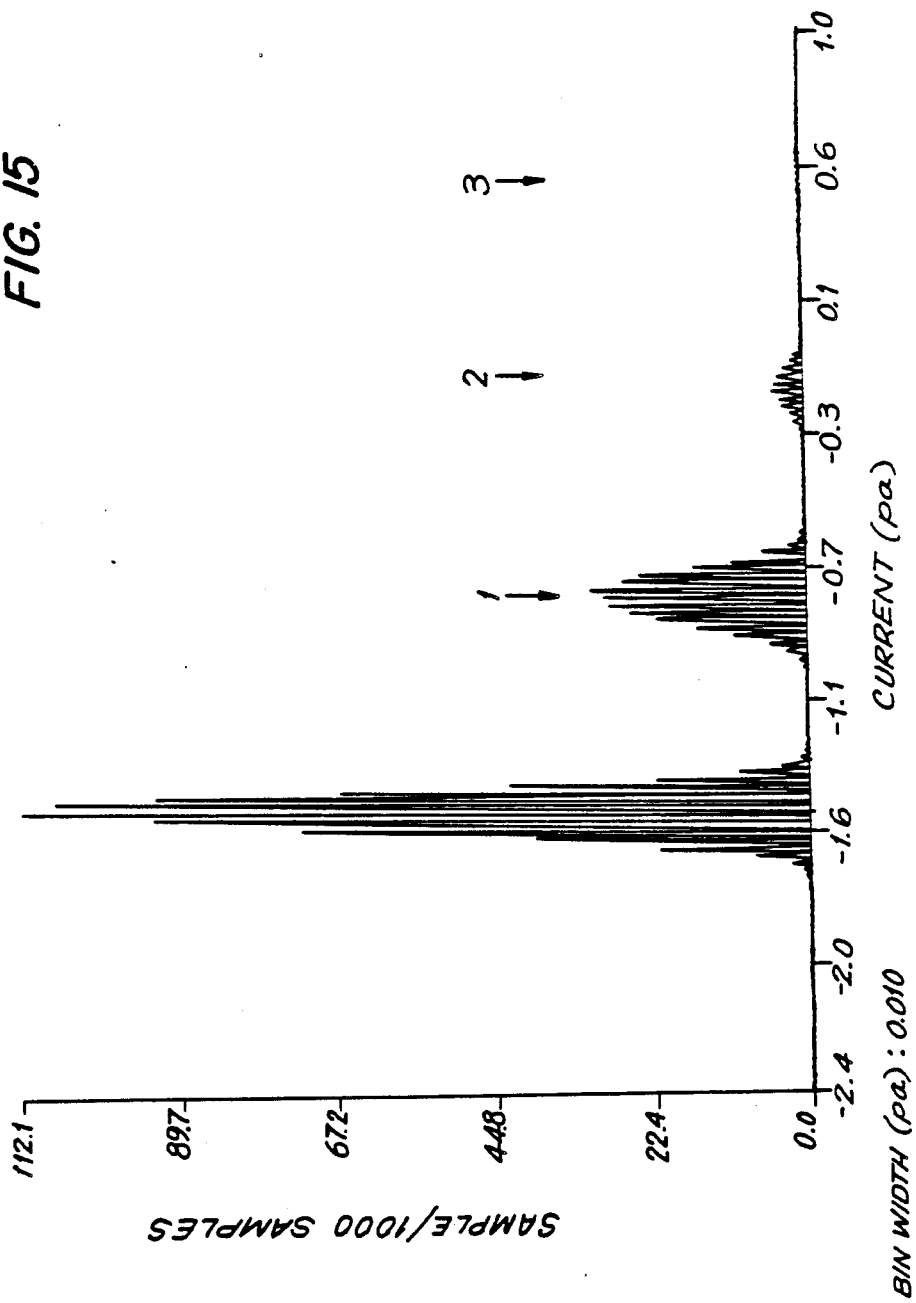
FIG. 15 is an amplitude distribution plot showing the frequency of occurrence of ionic current with a certain value due to the opening of three identical calcium channels of this invention reconstituted in a lipid bilayer.

The behavior of the calcium channel of the present invention at different potentials (0, −15 and −30 mV) is shown in FIG. 14B.

Both the mean open and mean closed times (i.e. mean duration of each opening or closing) of the calcium channels vary with the extent of depolarization (i.e. are voltage-dependent). At −60 mV (a typical cell potential) the channel is rarely open (not shown). As the voltage is moved in a depolarizing direction, the channel begins to exhibit both long and short duration openings separated by very long closures. With further depolarization, the long duration openings become more frequent and the short ones are prolonged. As a result, the mean-closed times are significantly reduced. With very large depolarizations, the channel clearly favors the open state (third tracing in FIG. 14B). This is illustrated in FIG. 16 which shows the mean open probability (FIG. 16A) as a function of the holding potential. The open probability reaches a maximum (about 0.7) at a potential slightly more positive than zero and a minimum at about −70 mV (not shown). The mean closed times range from 920 msec at −60 mV to less than 140 msec at potentials more positive than 0 mV. The overall mean open times ranged from 104 msec at −60 mV to 280 msec at 0 mV as shown in FIG. 17 which was obtained based on data from different experiments in which at least 200 openings were recorded at each potential within the range shown.

FIG. 18 was generated by multiplying the single channel currents by the opening probability at each potential. The result is an approximation of the macroscopic current which would have been consistent with macroscopic current measurements obtained previously for the high-threshold calcium channel in cerebellar Purkinje cells.

The i-V relationship shown in FIG. 19 was constructed from the single-channel data of the same type of experiments. FIG. 19 shows values obtained from 3 experiments. In the asymmetric solutions employed, the i-V relationship was nonlinear in the voltage range tested. From these data, the conductance of a single channel was estimated at 20 pS (slope of the linear portion of the i-V curve). The reversal potential was measured to be in the range of −90 mV to −120 mV which is consistent with the theoretical value of a barium-permeable channel.

Various known blockers of the neuronal calcium channels were tested for their effect on the reconstituted channels. Single channels were blocked by both cadmium and cobalt (at less than 100 micromolar) in the same manner as reported in Example 9. Single channels were also blocked by one microliter of whole *A.aperta* venom at 1:10 dilution.

(B) Fluorescence

Fluorescence emission spectra were obtained for the quin-2-loaded vesicles, as described in Example 8. The background fluorescence was first determined and later subtracted from the experimental values. Calcium chloride, in 10 microliter aliquots, was added directly into the quartz fluorescence cell and the fluorescence emission intensity was monitored at 475 nanometers. Fluorescence spectra were obtained on a modified Aminco-Bowman SPF spectrofluoro meter (Cherksey et al., *J. Membr. Biol.*, 84:105–116, 1985) but Perkin-Elmer (Plainfield, N.J.) equipment could have been used instead. Scattering and inner-filter corrections were made when appropriate.

The ability of the isolated protein to influence calcium ion uptake into liposomes was studied using vesicles preloaded with quin-2 as described in Example 8. In the absence of protein, little or no calcium entry into the vesicles was detected for at least 10 minutes following the addition of up to 6 mM of calcium ion to the bathing solution.

Figure 20:
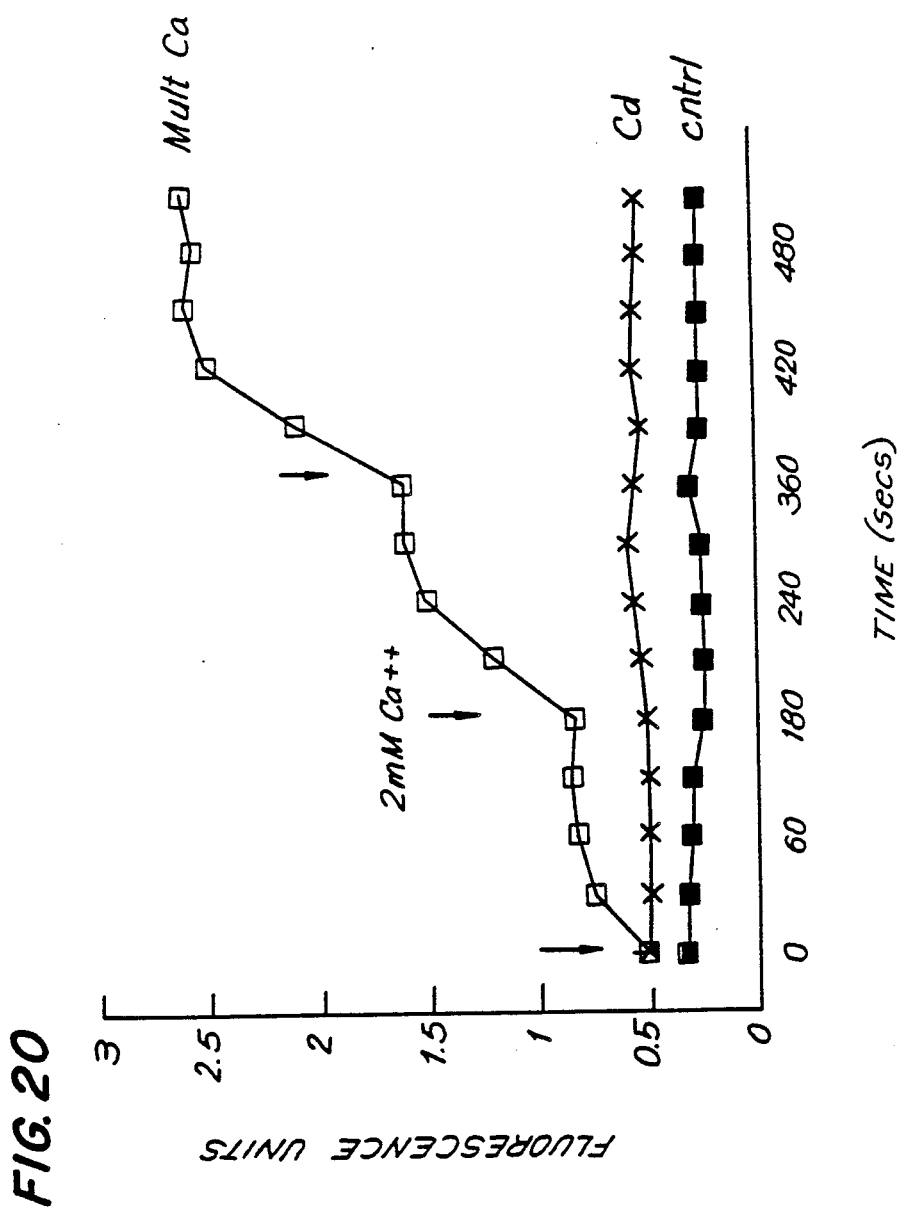

However, addition of calcium ion to the vesicle-containing solution was followed by a rapid and sustained increase in the intensity of quin-2 fluorescence as shown in FIG. 20 which is similar to FIG. 12. Calcium was added at 0, 180 and 360 seconds, each time to a final concentration of 2 mM. The uptake of calcium into the vesicles was blocked by cadmium ion at a concentration of 50 micromolar (shown by the X's).

Figure 21:
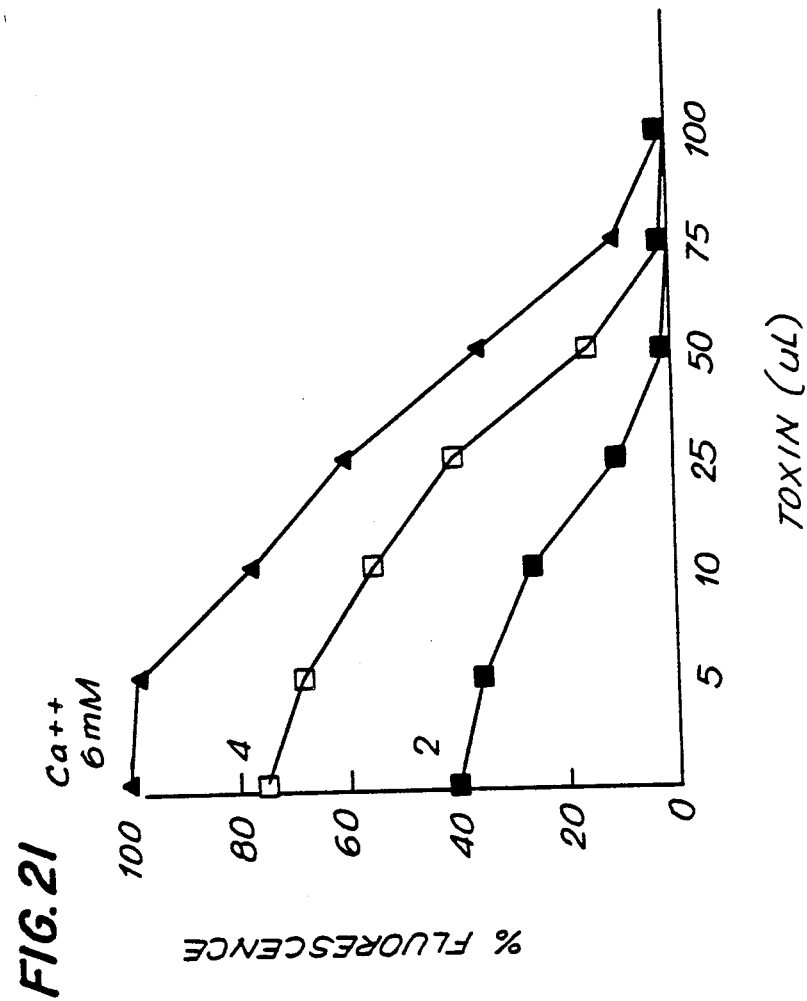
FIG. 21 is a plot of calcium channel blockage (inhibition of ionic current) by purified factor from *A.aperta* venom at various extravesicular calcium-ion concentrations.

In FIG. 21, purified *A.aperta* active factor obtained from spider venom at a 1:10 dilution was used to block the uptake of calcium at concentrations of 2, 4 and 6 mM. As expected from other experiments described herein, the effect was found to be dependent on both the dose of the active factor and on the external calcium concentration.

In another series of experiments, a membrane potential was established in the reconstituted vesicles by creating a potassium gradient across the vesicle membrane. The vesicles were then made permeable to K+ by the addition of $10^{-7}$M valinomycin. The potential could then be adjusted by the addition of potassium to the bathing solution.

Figure 22:
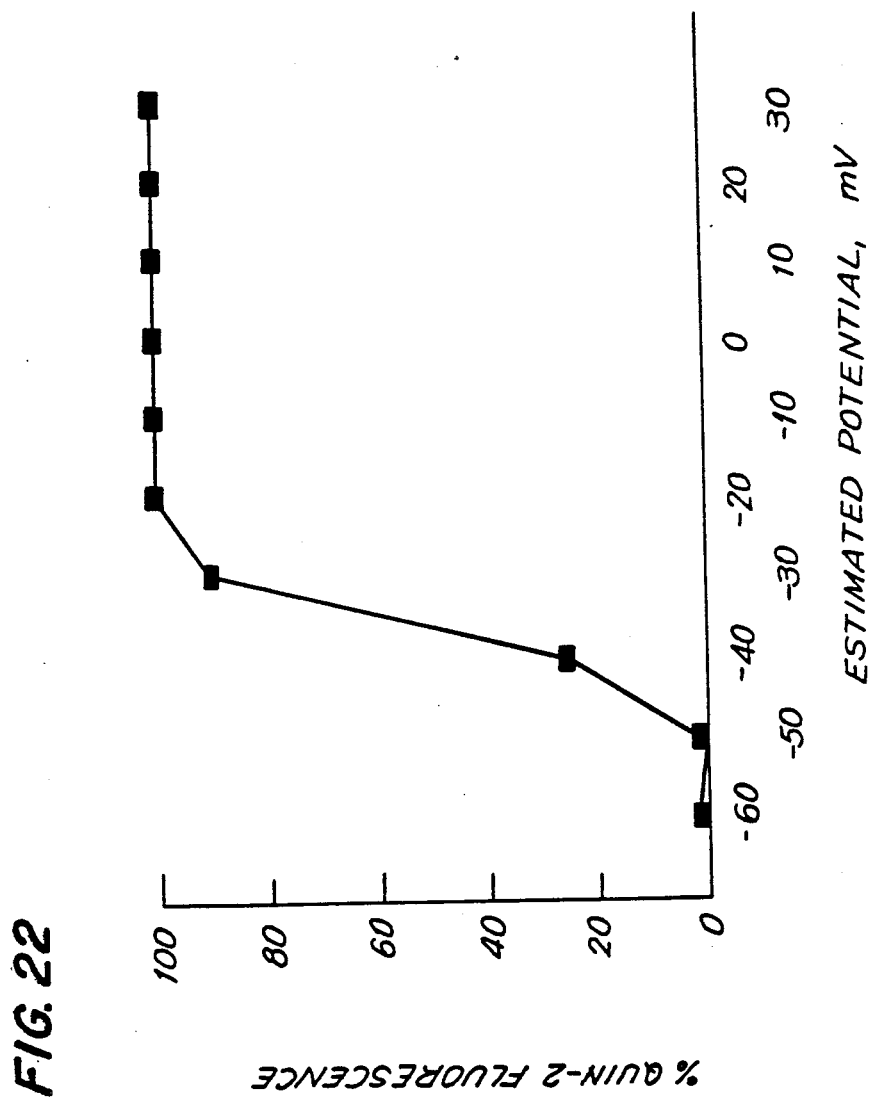

The voltage-dependent activation of the reconstituted protein was determined by measuring the increase in quin-2 fluorescence in the presence of 2 millinormal external calcium ion. As shown in FIG. 22, the entry of calcium ion increased sharply over a range of external-/internal potassium ratios (from 10:1 to 2:1) yielding calculated Nernst potentials ranging from −50 to +20 mV consistent with the known properties of the high-threshold neuronal calcium channel.

EXAMPLE 14

Electrophysiological Experiments on Squid Stellate Ganglia

Action potentials were induced by direct stimulation of the presynaptic nerve bundle of the giant synapse in squid stellate ganglia. The stimulation site was proximal to the recording electrode. The thus evoked presynaptic action potential is illustrated on the left of FIG. 23A (control). This in turn generated the usual postsynaptic potential which normally follows transmitter release from the presynaptic terminal to the postsynaptic terminal. Transmitter alters the permeability of the postsynaptic membrane to ions and causes the generation of the postsynaptic action potential.

Figure 23A:
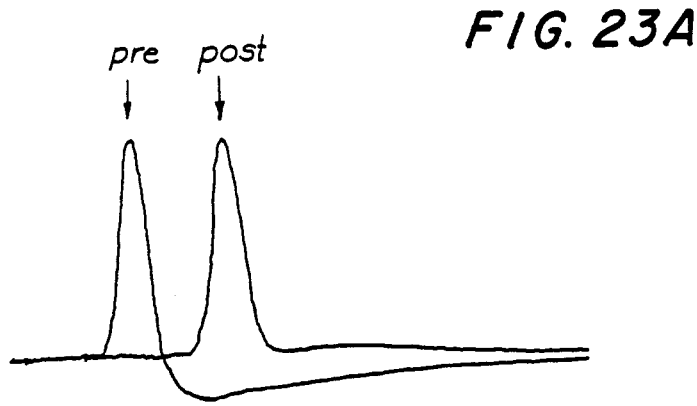
FIG. 23 depicts pre- and post-synaptic action potentials in the squid giant synapse in the absence (23A) and presence (23B) of partially purified *H.curta* venom extracellularly and a superimposition of the two (23C).
Figure 23B:
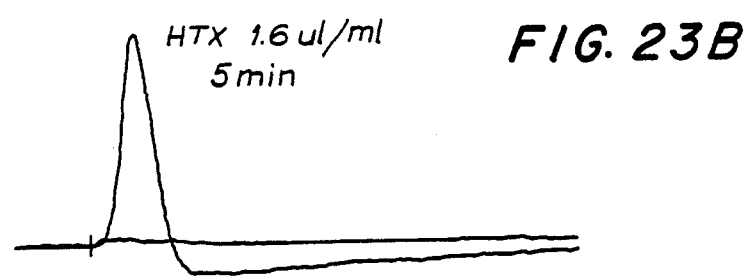
Figure 23C:
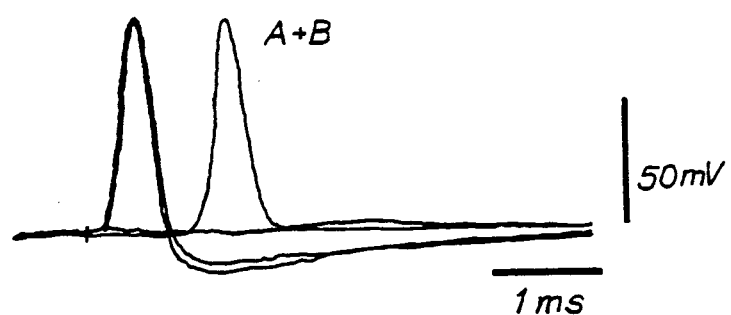

In the experiment that gave rise to FIG. 23B, partially purified venom of *H.curta* (i.e. the supernatant after separation of the precipitate of boiled venom) was introduced in the extracellular medium to a concentration of 1.6 microliters/ml five minutes before presynaptic stimulation as in FIG. 23A (concentrations of the calcium channel blocking factor may need to be adjusted depending on the depth of the synapse, the purity and dilution of the factor, etc. as is well known in the art). It can be observed that the presynaptic action potential is not different in FIG. 23B from that in FIG. 23A (this is confirmed in FIG. 23C which is a superimposition of 23A and 23B). However, in FIG. 23B the postsynaptic action potential is totally absent. From this experiment alone, (and without the benefit of other relevant portions of the present disclosure) it is not possible to tell whether the toxin blocked ionpermeability of the presynaptic membrane, release of transmitter from the presynaptic terminal, or ion-permeability of the postsynaptic membrane or a combination of these events. This was partially resolved using the voltage-clamp technique as described below and illustrated in FIG. 24.

Figure 24A:
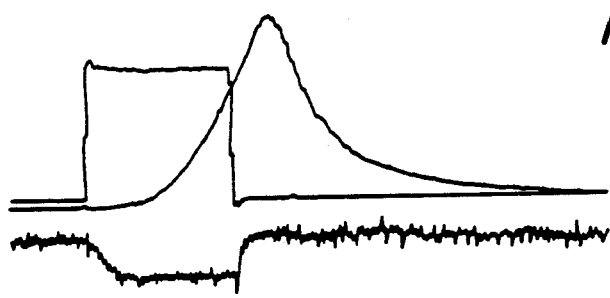
FIG. 24 depicts synaptic transmission in the same synapse under voltage-clamp conditions in the absence (24A) and presence (24B) of partially purified *A.aperta* venom and a superimposition of the two (24C).
Figure 24B:
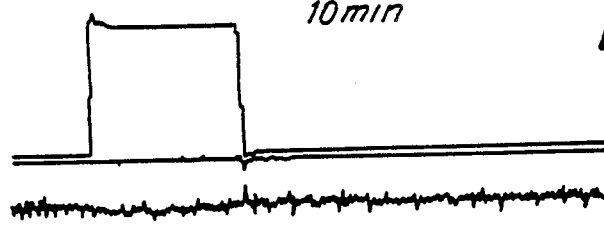
Figure 24C:
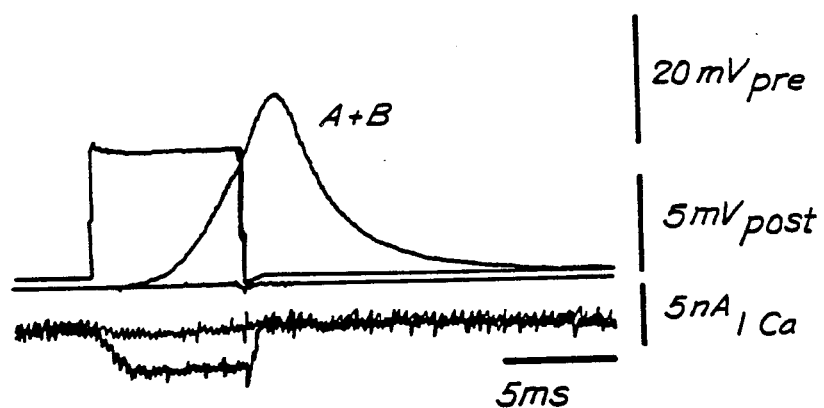

In the experiment that gave rise to FIG. 24, synaptic transmission was, evoked by depolarization of the presynaptic terminal. In FIG. 24A (control) sodium and potassium conductances were blocked with TTX and 3AP (3-aminopyridine) extracellularly and TEA intracellularly. Thus, the lower trace of the compensating current injected in the cell using the voltage-clamp circuitry is a measure of the presynaptic inward calcium current. The presynaptic step voltage generates a postsynaptic potential response.

Ten minutes after the application of partially purified *A.aperta* venom (illustrated in FIG. 24B) an identical presynaptic voltage step gives rise to neither a presynaptic calcium current nor a postsynaptic potential.

This indicates that the calcium channel blocking agent in this venom acts presynaptically by blocking the entry of calcium into the presynaptic cell (which would normally in turn trigger transmitter release). This is confirmed by FIG. 24C which is a superimposition of FIGS. 24A and B and demonstrates that no other events take place either presynaptically or postsynaptically.

In a third set of experiments, miniature end-plate potentials (MEPPS) were measured in end plate regions of squid giant synapse.

Partially purified *H.curta* venom was added to a concentration of 1.6 microliters/ml both in this and in the following experiment.

Figure 25:
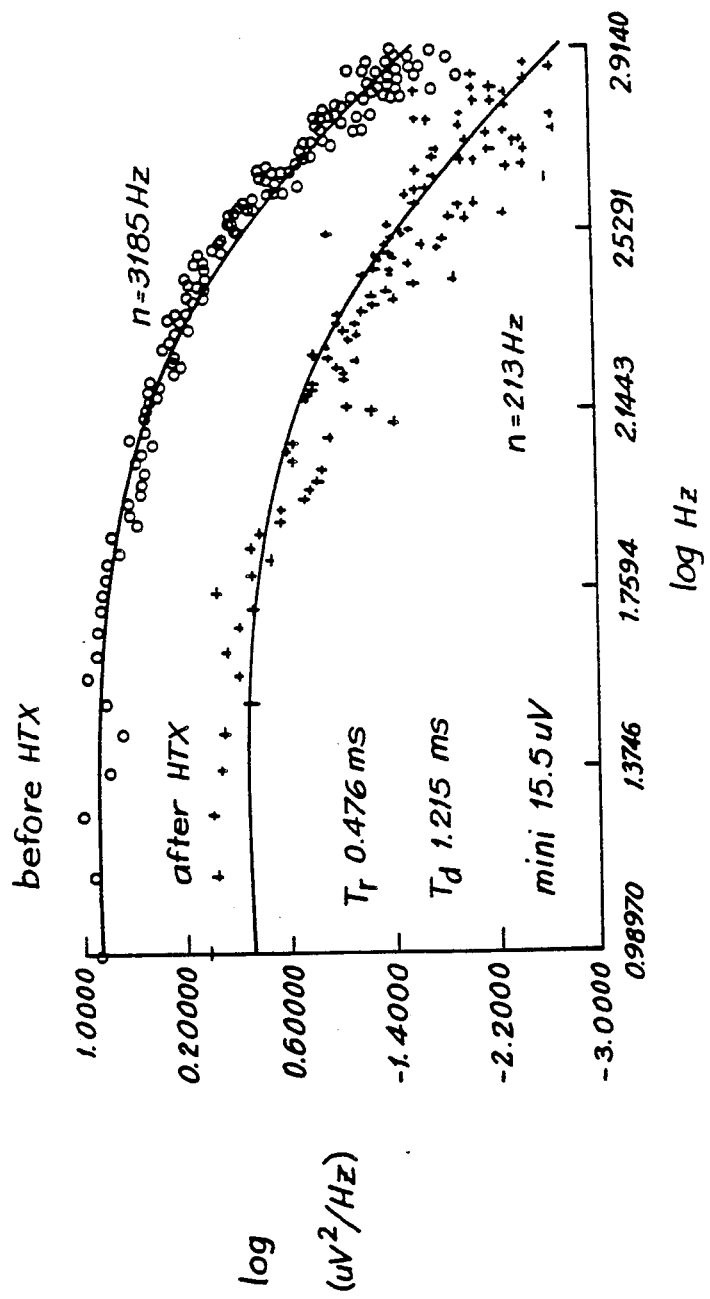
FIG. 25 is a power spectrum of miniature end-plate potentials as a function of the mean frequency of the miniature potentials in the absence and presence of extracellular partially purified *H.curta* venom.

FIG. 25 is a power spectrum of log of power density versus the mean frequency of the MEPPS. N represents the frequency of MEPPS occurrence (number of MEPPS/second). It can be seen that, upon introduction of *H.curta* venom in the bathing solution, n decreased more than one order of magnitude.

(In FIG. 25, Td and Tr are the decay and rise time constants of the fitted Lorenzians. The mean value of each miniature potential was 15.5 micro volts.)

The results described in this Example 14 are duplicated when the chromatography purified active factor is used instead of partially purified venom.

These results confirm that the spider venom (and the active factor present in it) impedes presynaptic transmitter release by interfering with passive calcium transport through the presynaptic membrane.

EXAMPLE 15

Isolation of the Calcium Channel from Squid Optic Lobe

Figure 26:
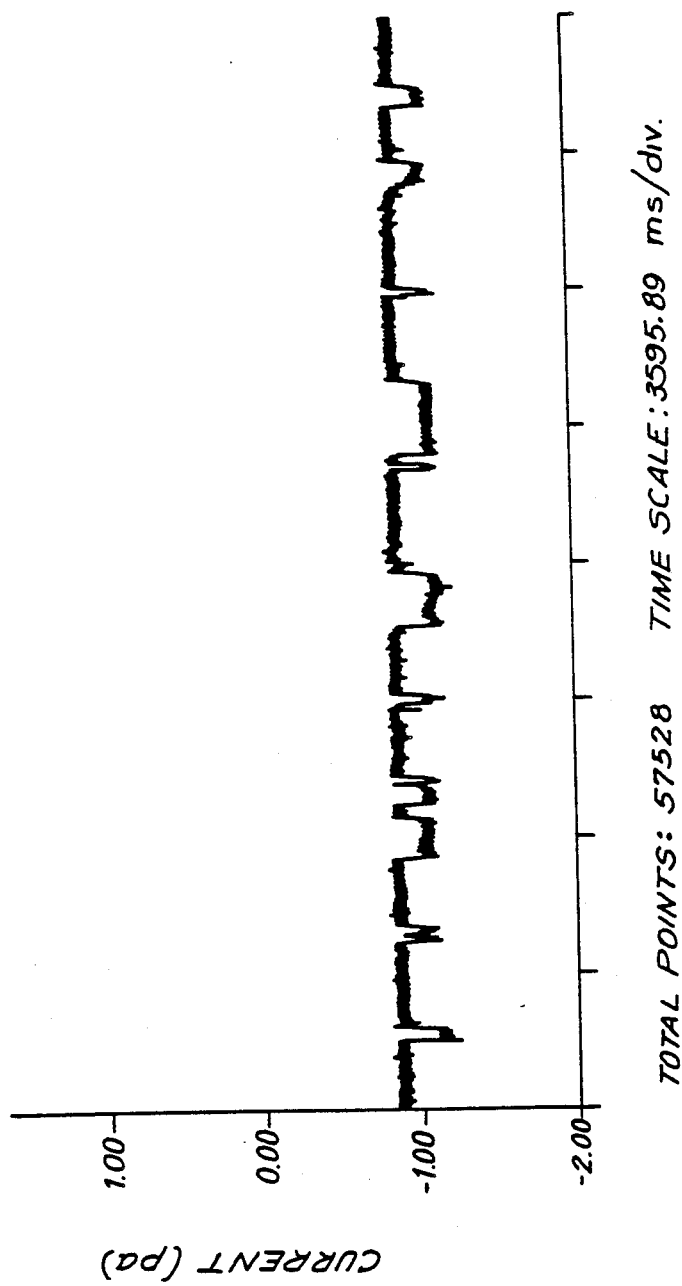
FIG. 26 is the same type of recording for calcium channels obtained from squid optic lobe.
Figure 27:
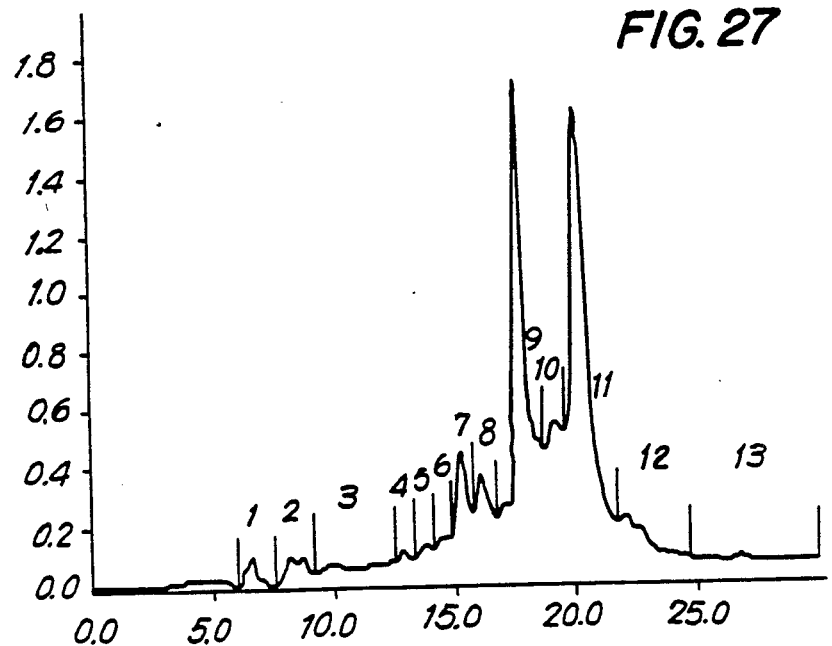
Figure 28:
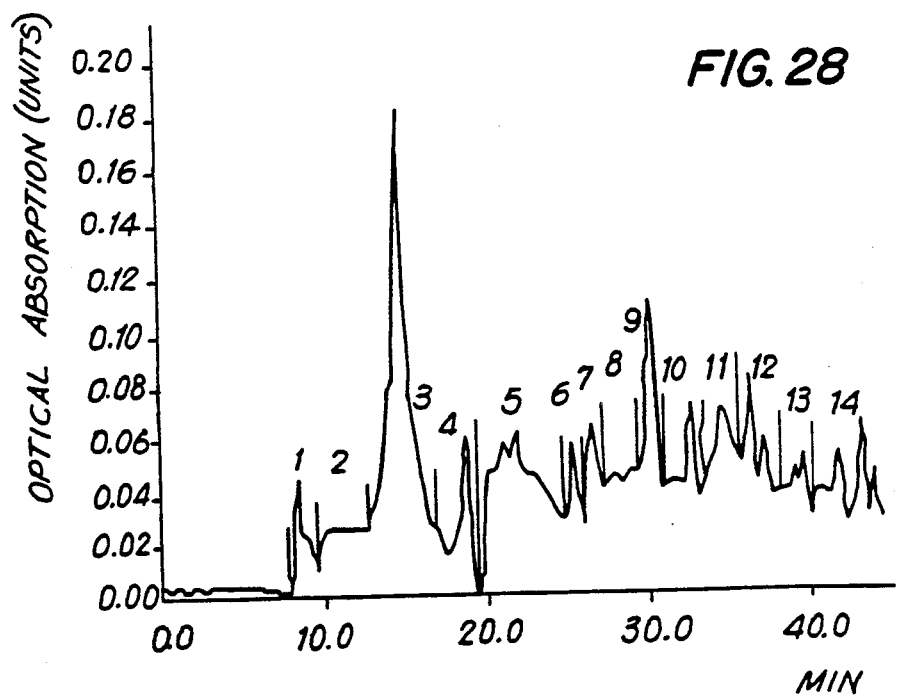

Squid Optic Lobe (5 g) was homogenized and subsequently processed in the manner of Example 7. The bilayer experiments (both fused and "tip-dip") of Example 8 were then repeated with the purified preparation optic lobe. The results were entirely consistent with the ones described above for the cerebellar calcium channels. The squid calcium channel had an estimated conductance of about 15 pS and its opening times were substantially longer as illustrated in FIG. 26.

EXAMPLE 16

Toxicity in Mammals

Mice were injected i.p. with 35, 15 and 3 microliters of boiled *A.aperta* venom. All of these doses were lethal within 3 to 30 minutes, depending on the dose administered. At 1, 0.5, and 0.1 microliter doses, all mice survived and recovered.

On observation, the symptoms exhibited by the injected mice were lethargy, absence of movement, respiratory symptoms of the type associated with brainstem dysfunction, and tremor. The symptoms attenuated in intensity and decreased in number with decreasing dose. Respiratory symptoms and tremor could be observed even in mice injected with 0.5 microliters of the partially purified (boiled) venom. At 0.1 microliter, no symptoms could be observed.

All of the foregoing symptoms indicate that the activity of the injected preparation is exerted on the central nervous system. This indication was reinforced by the absence of such peripheral effects as muscle paralysis, or cardiac arrest.

EXAMPLE 17

Isolation of Low-Threshold Calcium Channel Using Amiloride Gel

Guinea pig cerebellar material was processed as in Example 7. It was then purified according to the method of Example 8 except that the amiloride gel chromatography was performed after the factor-coupled gel chromatography. (The latter chromatographic purification was thus used to remove the high-threshold channel recognized by the active factor of the present invention.)

The low-threshold calcium channel was eluted from the amiloride gel using 400 mM sucrose, 10 mM HEPES (pH 7.4) containing 1 mM amiloride.

The channel activity of the thus-purified gel was tested as described above by the lipid bilayer technique. The channel has an estimated conductance of about 8 pS, is characterized by rapid openings (of the order of 1-100 msec at −0 mV), is rapidly inactivated (within about 1 sec at the same depolarization), and was blocked by cadmium (250micromolar).

In the manner described above, larger amounts of venom can be purified using chromatographic techniques and, after being coupled to a chromatography support, can be used as an affinity chromatography adsorbent for purification of larger amounts of calcium channels from brain material.

The calcium channel material purified using the calcium blocking factor of the present invention can be further purified by known chromatographic techniques, (e.g., using Sepharose) and the channel composition can be characterized (e.g., in terms of molecular weight, isoelectric point and homogeneity).

Preferably, large quantities of the active factor of the present invention will be first purified using a large G-15 column (e.g. 200 cm) followed by HPLC on a C-18 column or other HPLC column of the type used to effect organic separations. The thus purified factor may then be further characterized using well-known organic analytical chemistry techniques.

The thus purified factor may be coupled to an agarose support preferably following the procedure of Example, 6 and brain material can be first purified in an affinity column (preferably also large in size) using the active factor as the immuno-adsorbent. The thus isolated calcium channel material can be further purified by other chromatographic steps, such as chromatography on a G-25 column, wheat germ lectin affinity chromatography (or other lectin chromatography such as Concanavalin A), ion exchange chromatography (e.g. on diethylaminoethyl Sephadex) and combinations thereof. HPLC may be used as a final purification step, if necessary or appropriate.

The calcium channel protein of the present invention can be purified to homogeneity as tested by 2-dimensional SDS-PAGE, gel filtration, radioiodination/SDS-PAGE and other well-known techniques for determining homogeneity.

In parallel, SDS-PAGE under reducing and nonreducing conditions will help determine the presence of various subunits. The subunit responsible for binding to the venom-derived factor can be identified, e.g., by a binding assay using labelled factor. The subunit responsible for binding calcium can be identified by a well-known calcium binding assay, such as one using lanthanites.

Partial (or total) sequence information can be obtained, and/or monoclonal antibodies can be raised preferably using the thus purified calcium channel composition as the initial immunogen both according to techniques well-known in the art. If partial sequence information is obtained, it can be used to construct nucleic acid probes useful in identifying positive recombinant clones expressing calcium channel protein. Similarly, the monoclonal antibodies may be used to screen such clones for immunoaffinity purification of native or recombinant channel protein.

The entire calcium channel protein sequence can be identified either by directly sequencing the purified native channel protein or by sequencing the expression products of recombinant organisms incorporating calcium channel nucleic acid, using well-known methods.

What is claimed is:

1. A purified calcium channel protein, said channel being of the type that is responsible for calcium conductance in central neurons.

2. The protein of claim 1, wherein said conductance is low-threshold calcium conductance.

3. The protein of claim 1, wherein said conductance is high-threshold calcium conductance.

4. The protein of claim 2 purified by extraction from cell membrane material on an affinity chromatography medium comprising as an affinity adsorbent a calcium channel blocking factor present in funnel-web spider venom covalently bonded to a monosaccharide or polysaccharide support.

5. The protein of claim 2, wherein said conductance is dihydropyridine-resistant.

6. The protein of claim 5, wherein said neurons are Purkinje cells.

7. The protein of claim 5, wherein said neurons are squid stellate ganglia.

8. The protein of claim 3 further characterized by specific binding to a member selected from the group consisting of venom of funnel-web spiders and calcium-channel blocking factors isolated from said venom.

9. The protein of claim 8, wherein said spiders are selected from the group consisting of *Agelenopsis aperta, Hololena curta* and Calilena.

10. The protein of claim 4, wherein said member is a hydrophilic nonpolypeptide calcium-channel blocking factor having a molecular weight below 700 daltons and is extracted from said venom by column chromatography.

11. The protein of claim 10, wherein said factor has a molecular weight between about 300 and about 500 daltons as measured by column chromatography.

12. A method for purifying mammalian cell membrane calcium channels of the type responsible for calcium conductance in central neurons, comprising subjecting an impure preparation of said channels to affinity chromatography using, as an affinity adsorbent, a calcium-channel blocking factor, which specifically and reversibly blocks said channels and is isolated from funnel-web spider venom, said factor being covalently bonded to a monosaccharide or polysaccharide chromatography support medium, thereby causing said channels to bind to said affinity adsorbent while excluding impurities;
eluting said channels from said factor covalently bound to said chromatographic support medium; and
recovering said channels in purified form.

13. The method of claim 12, wherein said factor is a hydrophilic nonpolypeptide substance having a molecular weight of less than 700 daltons as measured by column chromatography.

14. The method of claim 13, wherein said molecular weight is within the range of about 300 to about 500 daltons as measured by column chromatography.

15. A method for regulating calcium transport across a cell membrane possessing calcium channels of the type responsible for high-threshold calcium conductance in central neurons comprising exposing said cell membrane to a nonpolypeptide calcium channel blocking factor isolated from funnel-web spider venom and having an apparent molecular weight of less than 700 daltons based on column chromatography, thereby causing said factor to bind to the calcium channels and selectively block calcium ion transport through said channels.

16. A method according to claim 40, wherein said cell membrane is a neuron cell membrane.

17. The method of claim 15, wherein said factor is isolated from the venom of at least one spider species selected from the group consisting of *Agelenopsis aperta, Hololena curta* and Calilena.

18. The method of claim 17, wherein said factor is employed at a concentration equal to the concentration of said factor in $0.625 \times 10^{-3}$ microliters of said venom per ml of extracellular medium.

19. The method of claim 17, wherein said factor is employed at a concentration at least of the order of $10^{-8}$M in the extracellular medium.

20. A method for blocking calcium channels of the type responsible for high-threshold calcium conductance in a cell membrane comprising exposing a cell to a concentration of a calcium channel blocking factor isolated from the venom of funnel-web spiders and having a molecular weight of less than 700 daltons at a concentration sufficient to extinguish said calcium conductance.

21. A method according to claim 20, wherein said cell is a central neuron.

22. A method for blocking calcium channels responsible for high-threshold calcium conductance of neuronal membranes comprising exposing neurons to venom from Calilena funnel-web spider.

23. A method for blocking calcium channels responsible for high-threshold calcium conductance of cell membranes comprising exposing cells to a nonpolypeptide calcium channel blocking factor isolated from the venom of funnel-web spiders by column chromatography and having an apparent molecular weight of less than 700 daltons.

24. The method of claim 23, wherein said factor is isolated from the venom of *Agelenopsis aperta*.

25. A hydrophilic nonpolypeptide calcium conductance-blocking factor isolated from the venom of funnel web spiders by column chromatography and having an apparent molecular weight of no more than 700 daltons.

26. The factor of claim 25 isolated from the venom of *Agelenopsis aperta* and having a molecular weight within the range of 300 to 500 daltons.

27. The factor of claim 25 isolated by column chromatography of the boiling-resistant fraction of said venom on alpha-linked dextran polysaccharide affinity chromatographic medium.

28. The factor of claim 27 resolved on said chromatography by means of a saline buffer.

29. The factor of claim 28 collected in the fractions collected from said chromatography.

30. The factor of claim 29 wherein said saline buffer contains 0.5M NaCl.

31. The factor of claim 30 wherein said venom is selected from the group consisting of *Hololena curta, Agelenopsis aperta* and Calilena spider venom and mixtures thereof.

32. A method for blocking transmitter release resulting from the activation of high-threshold calcium channels of the type present in central neurons in a neuronal synapse comprising exposing said synapse to a calcium-channel blocking agent wherein said agent is a hydrophilic nonpolypeptide calcium conductance-blocking factor isolated from the venom of funnel web spiders by column chromatography and having an apparent molecular weight of no more than 700 daltons and issued in an extracellular amount effective to block the high-threshold calcium channels of the presynaptic neuron and thereby inhibit a presynaptic calcium current in said neuron.

33. The method of claim 32, wherein said factor has a molecular weight within the range of about 300 to about 500 daltons.

* * * * *